United States Patent
Carl et al.

(10) Patent No.: US 8,043,345 B2
(45) Date of Patent: Oct. 25, 2011

(54) DEVICE AND METHOD FOR CORRECTING A SPINAL DEFORMITY

(75) Inventors: Allen L. Carl, Slingerlands, NY (US); Dan Sachs, Minneapolis, MN (US)

(73) Assignees: K Spine, Inc., Minnetonka, MN (US); Albany Medical College, Albany, NY (US)

( * ) Notice: Subject to any disclaimer, the term of this patent is extended or adjusted under 35 U.S.C. 154(b) by 0 days.

(21) Appl. No.: 12/645,305

(22) Filed: Dec. 22, 2009

(65) Prior Publication Data

US 2010/0100133 A1 Apr. 22, 2010

Related U.S. Application Data

(62) Division of application No. 11/196,952, filed on Aug. 3, 2005, now Pat. No. 7,658,753.

(60) Provisional application No. 60/598,882, filed on Aug. 3, 2004.

(51) Int. Cl.
*A61B 17/70* (2006.01)
(52) U.S. Cl. .......... 606/279; 606/246; 606/263
(58) Field of Classification Search .......... 606/60, 606/257, 264, 279, 53–59, 246, 263
See application file for complete search history.

(56) References Cited

U.S. PATENT DOCUMENTS

| | | | |
|---|---|---|---|
| 2,774,350 A | 9/1952 | Cleveland | |
| 3,242,922 A | 3/1966 | Thomas | |
| 3,648,691 A | 3/1972 | Lumb et al. | |
| 3,693,616 A | 9/1972 | Roaf et al. | |
| 3,865,105 A | 2/1975 | Lode | |
| 4,024,588 A | 5/1977 | Janssen et al. | |
| 4,078,559 A | 3/1978 | Nissinen | |
| 4,269,178 A | 5/1981 | Keene | |
| 4,274,401 A | 6/1981 | Miskew | |
| 4,355,645 A | 10/1982 | Mitani | |
| 4,361,141 A | 11/1982 | Tanner | |
| 4,369,769 A | 1/1983 | Edwards | |
| 4,404,967 A | 9/1983 | Bacal et al. | |
| 4,411,259 A | 10/1983 | Drummond | |
| 4,448,191 A | 5/1984 | Rodnyansky et al. | |

(Continued)

FOREIGN PATENT DOCUMENTS

EP 0260044 3/1988

(Continued)

OTHER PUBLICATIONS

International Search Report dated Oct. 2, 2008 for PCT/US 08/65979.

*Primary Examiner* — Eduardo C Robert
*Assistant Examiner* — Ellen C Hammond
(74) *Attorney, Agent, or Firm* — Knobbe Martens Olson & Bear LLP

(57) ABSTRACT

A method for correcting a spinal deformity is provided. A spinal implant for correcting a spinal deformity includes a multipoint connector that connects to at least one vertebra of a spine at a plurality of locations and a force directing device that applies a force to the vertebra through the multipoint connector. The force directing device may include a rod which extends generally along an axis of the spine and a force directing member which is adjustably coupled to both the rod and the multipoint connector and which applies a corrective force to the at least one vertebra.

36 Claims, 24 Drawing Sheets

U.S. PATENT DOCUMENTS

| | | | |
|---|---|---|---|
| 4,505,268 A | 3/1985 | Sgandurra | |
| 4,573,454 A | 3/1986 | Hoffman | |
| 4,611,582 A | 9/1986 | Duff | |
| 4,697,582 A | 10/1987 | William | |
| 4,738,251 A | 4/1988 | Plaza | |
| 4,773,402 A | 9/1988 | Asher et al. | |
| 4,805,602 A | 2/1989 | Puno et al. | |
| 4,815,453 A | 3/1989 | Cotrel | |
| 5,000,166 A | 3/1991 | Karpf | |
| 5,011,484 A | 4/1991 | Breard | |
| 5,030,220 A | 7/1991 | Howland | |
| 5,084,049 A | 1/1992 | Asher et al. | |
| 5,092,867 A | 3/1992 | Harms et al. | |
| 5,127,912 A | 7/1992 | Ray et al. | |
| 5,133,716 A | 7/1992 | Plaza | |
| 5,176,679 A | 1/1993 | Lin | |
| 5,196,014 A | 3/1993 | Lin | |
| 5,219,349 A | 6/1993 | Krag et al. | |
| 5,242,443 A | 9/1993 | Kambin | |
| 5,257,994 A | 11/1993 | Lin | |
| 5,306,275 A | 4/1994 | Bryan | |
| 5,330,474 A | 7/1994 | Lin | |
| 5,366,455 A | 11/1994 | Dove et al. | |
| 5,382,248 A | 1/1995 | Jacobson et al. | |
| 5,387,212 A | 2/1995 | Yuan et al. | |
| 5,387,213 A | 2/1995 | Breard et al. | |
| 5,391,168 A | 2/1995 | Sanders et al. | |
| 5,397,363 A | 3/1995 | Gelbard | |
| 5,413,576 A | 5/1995 | Rivard | |
| 5,436,542 A | 7/1995 | Petelin et al. | |
| 5,437,669 A | 8/1995 | Yuan et al. | |
| 5,437,671 A | 8/1995 | Lozier et al. | |
| 5,456,722 A | 10/1995 | McLeod et al. | |
| 5,470,333 A | 11/1995 | Ray | |
| 5,480,440 A | 1/1996 | Kambin | |
| 5,490,851 A | 2/1996 | Nenov et al. | |
| 5,496,318 A | 3/1996 | Howland et al. | |
| 5,498,262 A | 3/1996 | Bryan | |
| 5,540,689 A | 7/1996 | Sanders et al. | |
| 5,549,679 A | 8/1996 | Kuslich | |
| 5,562,660 A | 10/1996 | Grob | |
| 5,562,662 A | 10/1996 | Brumfield et al. | |
| 5,569,246 A | 10/1996 | Ojima et al. | |
| 5,586,983 A | 12/1996 | Sanders et al. | |
| 5,591,165 A | 1/1997 | Jackson | |
| 5,611,800 A | 3/1997 | Davis et al. | |
| 5,645,599 A | 7/1997 | Samani | |
| 5,649,926 A | 7/1997 | Howland | |
| 5,672,175 A | 9/1997 | Martin | |
| 5,702,395 A | 12/1997 | Hopf | |
| 5,702,452 A | 12/1997 | Argenson et al. | |
| 5,704,936 A | 1/1998 | Mazel | |
| 5,725,582 A | 3/1998 | Bevan et al. | |
| 5,728,097 A | 3/1998 | Matthews | |
| 5,733,284 A | 3/1998 | Martin | |
| 5,782,831 A | 7/1998 | Sherman et al. | |
| 5,797,910 A * | 8/1998 | Martin | 606/57 |
| 5,814,046 A | 9/1998 | Hopf | |
| 5,928,232 A | 7/1999 | Howland et al. | |
| 5,938,663 A | 8/1999 | Petreto | |
| 5,989,256 A | 11/1999 | Kuslich et al. | |
| 6,015,409 A | 1/2000 | Jackson | |
| 6,086,590 A | 7/2000 | Margulies et al. | |
| 6,132,431 A | 10/2000 | Nilsson et al. | |
| 6,136,000 A | 10/2000 | Louis et al. | |
| 6,176,861 B1 | 1/2001 | Bernstein et al. | |
| 6,277,120 B1 | 8/2001 | Lawson | |
| 6,293,949 B1 | 9/2001 | Justis et al. | |
| 6,296,643 B1 | 10/2001 | Hopf et al. | |
| 6,299,613 B1 | 10/2001 | Ogilvie et al. | |
| 6,325,805 B1 | 12/2001 | Ogilvie et al. | |
| 6,358,254 B1 | 3/2002 | Anderson | |
| 6,364,883 B1 | 4/2002 | Santilli | |
| 6,391,030 B1 | 5/2002 | Wagner et al. | |
| 6,423,065 B2 | 7/2002 | Ferree | |
| 6,451,019 B1 | 9/2002 | Zucherman et al. | |
| 6,458,131 B1 | 10/2002 | Ray | |
| 6,514,255 B1 | 2/2003 | Ferree | |
| 6,537,276 B2 | 3/2003 | Metz Stavenhagen | |
| 6,547,789 B1 | 4/2003 | Ventre et al. | |
| 6,551,320 B2 | 4/2003 | Lieberman | |
| 6,554,831 B1 | 4/2003 | Rivard et al. | |
| 6,565,605 B2 | 5/2003 | Goble et al. | |
| 6,579,319 B2 | 6/2003 | Goble et al. | |
| 6,582,433 B2 | 6/2003 | Yun | |
| 6,589,243 B1 | 7/2003 | Viart et al. | |
| 6,610,091 B1 | 8/2003 | Reiley | |
| 6,616,669 B2 | 9/2003 | Ogilvie et al. | |
| 6,623,484 B2 | 9/2003 | Betz et al. | |
| 6,626,909 B2 | 9/2003 | Chin | |
| 6,641,585 B2 | 11/2003 | Sato et al. | |
| 6,645,207 B2 | 11/2003 | Dixon et al. | |
| 6,669,729 B2 | 12/2003 | Chin | |
| 6,682,533 B1 | 1/2004 | Dinsdale et al. | |
| 6,709,435 B2 | 3/2004 | Lin | |
| 6,755,828 B2 | 6/2004 | Shevtsov et al. | |
| 6,773,437 B2 | 8/2004 | Ogilvie et al. | |
| 6,802,844 B2 | 10/2004 | Ferree | |
| 6,811,567 B2 | 11/2004 | Reiley | |
| 6,946,000 B2 | 9/2005 | Senegas et al. | |
| 6,966,930 B2 | 11/2005 | Arnin et al. | |
| 6,986,771 B2 | 1/2006 | Paul et al. | |
| 7,018,379 B2 | 3/2006 | Drewry et al. | |
| 7,029,475 B2 | 4/2006 | Panjabi | |
| 7,048,736 B2 | 5/2006 | Robinson et al. | |
| 7,074,237 B2 | 7/2006 | Goble et al. | |
| 7,087,056 B2 | 8/2006 | Vaughan | |
| RE39,325 E | 10/2006 | Bryan | |
| 7,128,743 B2 | 10/2006 | Metz Stavenhagen | |
| 7,220,262 B1 | 5/2007 | Hynes | |
| 7,335,203 B2 | 2/2008 | Winslow et al. | |
| 7,338,490 B2 | 3/2008 | Ogilvie et al. | |
| 7,367,978 B2 | 5/2008 | Drewry et al. | |
| 7,481,828 B2 | 1/2009 | Mazda et al. | |
| 7,524,324 B2 | 4/2009 | Winslow et al. | |
| 2002/0055739 A1 | 5/2002 | Lieberman | |
| 2002/0133155 A1 | 9/2002 | Ferree | |
| 2002/0143329 A1 | 10/2002 | Serhan et al. | |
| 2002/0151978 A1 | 10/2002 | Zacouto et al. | |
| 2003/0040746 A1 | 2/2003 | Mitchell et al. | |
| 2003/0093117 A1 | 5/2003 | Saadat | |
| 2003/0109881 A1 | 6/2003 | Shirado et al. | |
| 2003/0153915 A1 | 8/2003 | Nekozuka et al. | |
| 2003/0220643 A1 | 11/2003 | Ferree | |
| 2004/0006391 A1 | 1/2004 | Reiley | |
| 2004/0097931 A1 | 5/2004 | Mitchell et al. | |
| 2004/0106921 A1 * | 6/2004 | Cheung et al. | 606/61 |
| 2004/0149065 A1 | 8/2004 | Moran | |
| 2004/0167520 A1 | 8/2004 | Zucherman et al. | |
| 2005/0033295 A1 | 2/2005 | Wisnewski | |
| 2005/0043797 A1 | 2/2005 | Lee | |
| 2005/0049705 A1 | 3/2005 | Hale et al. | |
| 2005/0055096 A1 | 3/2005 | Serhan et al. | |
| 2005/0080420 A1 | 4/2005 | Farris et al. | |
| 2005/0149030 A1 | 7/2005 | Serhan et al. | |
| 2005/0154390 A1 | 7/2005 | Biedermann et al. | |
| 2005/0203509 A1 | 9/2005 | Chinnaian et al. | |
| 2005/0203511 A1 | 9/2005 | Wilson-MacDonald et al. | |
| 2005/0209603 A1 | 9/2005 | Zucherman et al. | |
| 2005/0216004 A1 | 9/2005 | Schwab | |
| 2005/0228326 A1 | 10/2005 | Kalfas et al. | |
| 2005/0228377 A1 | 10/2005 | Chao et al. | |
| 2005/0234453 A1 | 10/2005 | Shaolian et al. | |
| 2005/0245929 A1 | 11/2005 | Winslow et al. | |
| 2005/0261770 A1 | 11/2005 | Kuiper et al. | |
| 2005/0267470 A1 | 12/2005 | McBride | |
| 2006/0047282 A1 | 3/2006 | Gordon | |
| 2006/0064091 A1 | 3/2006 | Ludwig et al. | |
| 2006/0084996 A1 | 4/2006 | Metz Stavenhagen | |
| 2006/0271050 A1 | 11/2006 | Piza Vallespir | |
| 2007/0073293 A1 | 3/2007 | Martz et al. | |
| 2007/0233093 A1 | 10/2007 | Falahee | |

FOREIGN PATENT DOCUMENTS

| | | |
|---|---|---|
| EP | 0322334 | 6/1989 |
| EP | 0418387 | 3/1991 |
| EP | 1281361 | 2/2003 |

| | | | | | |
|---|---|---|---|---|---|
| FR | 2697744 | 5/1994 | RU | 888968 A1 | 1/1979 |
| FR | 2736535 | 1/1997 | WO | WO 92/13496 A1 | 8/1992 |
| FR | 2781359 | 1/2000 | WO | WO 2006/010844 A1 | 2/2006 |
| FR | 2801492 | 6/2001 | WO | WO 2007/051924 A1 | 5/2007 |
| GB | 780652 | 7/1955 | | | |

* cited by examiner

DEVICE AND METHOD FOR CORRECTING A SPINAL DEFORMITY

CROSS-REFERENCE TO RELATED APPLICATIONS

The present application is a divisional of application Ser. No. 11/196,952, filed Aug. 3, 2005 and entitled "Device and Method for Correcting a Spinal Deformity," which claims the benefit of U.S. Provisional Application No. 60/598,882, filed Aug. 3, 2004 and entitled "Spine Treatment Devices and Methods," the disclosure of each of which is hereby incorporated by reference in its entirety.

BACKGROUND OF THE INVENTION

1. Field of the Invention

The invention relates to devices to treat the spine, including but not limited to spinal stabilization devices, dynamic stabilizers, spinal deformity correction devices, devices to treat pain associated with the spine, and other spinal treatment devices.

2. Description of the Related Art

Certain spine conditions, defects, deformities (e.g., scoliosis) as well as injuries may lead to structural instabilities, nerve or spinal cord damage, pain or other manifestations. Back pain (e.g., pain associated with the spinal column or mechanical back pain) may be caused by structural defects, by injuries or over the course of time from the aging process. For example, back pain is frequently caused by repetitive and/or high stress loads on or increased motion around certain honey or soft tissue structures. The natural course of aging leads to degeneration of the disc, loss of disc height, and instability of the spine among other structural manifestations at or around the spine. With disc degeneration, the posterior elements of the spine bear increased loads with disc height loss, and subsequently attempt to compensate with the formation of osteophytes and thickening of various stabilizing spinal ligaments. The facet joints may develop pain due to arthritic changes caused by increased loads. Furthermore, osteophytes in the neural foramina and thickening of spinal ligaments can lead to spinal stenosis, or impingement of nerve roots in the spinal canal or neural foramina. Scoliosis may also create disproportionate loading on various elements of the spine and may require correction, stabilization or fusion.

Pain caused by abnormal motion of the spine has long been treated by fixation of the motion segment. Spinal fusion is one way of stabilizing the spine to reduce pain. In general, it is believed that anterior interbody or posterior fusion prevents movement between one or more joints where pain is occurring from irritating motion. Fusion typically involves removal of the native disc, packing bone graft material into the resulting intervertebral space, and anterior stabilization, e.g., with intervertebral fusion cages or posterior stabilization, e.g., supporting the spinal column with internal fixation devices such as rods and screws. Internal fixation is typically an adjunct to attain intervertebral fusion. Many types of spine implants are available for performing spinal fixation, including the Harrington hook and rod, pedicle screws and rods, interbody fusion cages, and sublaminar wires.

Spinal stenosis pain or from impingement of nerve roots in the neural foramina has been treated by laminectomy and foraminotomy, and sometimes reinforced with rod and screw fixation of the posterior spine. More recently, surgeons have attempted to relieve spinal stenosis by distracting adjacent spinous processes with a wedge implant. Pain due to instability of the spine has also been treated with dynamic stabilization of the posterior spine, using elastic bands that connect pedicles of adjacent vertebrae.

The typical techniques for fusion, distraction, decompression, and dynamic stabilization require open surgical procedures with removal of stabilizing muscles from the spinal column, leading to pain, blood loss, and prolonged recovery periods after surgery due in part to the disruption of associated body structures or tissue during the procedures.

To reduce the invasiveness of fusion procedures, some methods of fusion have been proposed that do not require the extensive stripping of muscles away from the spinal column of earlier approaches. These involve posteriorly or laterally accessing the spine and creating spaces adjacent the spine for posterior stabilization. Some of these procedures include fusion via small working channels, created with dilator type devices or an external guide to create a trajectory channel between two ipsilateral neighboring pedicle screws. Also, placing support structures between adjacent pedicle screws and across a joint requires accessing and working in an area from a difficult angle (the support structure is typically oriented somewhat perpendicular to an angle of access and through muscle and connective tissue). Furthermore, these stabilization devices typically involve the use of 4 pedicle screws (each having a risk associated with it when placed in the spine), two on each side of a motion segment, and are not ideally suited for percutaneous stabilization required across more than one or two segments. Accordingly, it would be desirable to provide a less invasive or less disruptive segmental spine stabilization procedure and implant that has a reduced risk of damage or injury to associated tissue. It would also be desirable to provide an implanted posterior spine system that may be used to stabilize more than two motion segments in a less disruptive or less invasive manner.

One method of fusing a vertebra has been proposed using bilateral screws through the lamina using a posterior approach. However, geometric placement of the device is difficult and the procedure is considered dangerous because the laminar screws could enter through anteriorly into the spinal canal and cause nerve damage.

Accordingly, it would be desirable to provide a device that reduces the difficulties risks of the current procedures. It would also be desirable to provide a device that can be placed in a less disruptive or less invasive manner than commonly used procedures.

Unintended consequences of fixation include stress shielding of bone, as well as transfer of load to adjacent, still dynamic motion segments, and eventual degeneration of adjacent motion segments. Flexible stabilization of motion segments with plastic, rubber, super-elastic metals, fabric, and other elastic materials has been proposed to provide a degree of dynamic stabilization of some joints. Many of these constructs are not load bearing. Dynamic stabilization from pedicle screw to pedicle screw along the length of the spine has been proposed. However, this device has the disadvantage of requiring placement of 4 pedicle screws and associated tissue disruption.

Due to the risks, inconvenience, and recovery time required for surgical implantation of spinal devices, some patients may continue to prefer rigid fixation of a painful or degenerative motion segment over dynamic stabilization of the joint. In addition, doctors may be reluctant to recommend dynamic stabilization for patients with back pain, because it may not alleviate pain to a patient's satisfaction.

Furthermore, even in patients who experience good relief of pain with dynamic stabilizers, it is anticipated that while the onset of arthritic changes may be deferred, many patients will still eventually proceed to develop degeneration, and require fixation of the motion segment to obtain pain relief. Repeat spine procedures to remove one implant and replace it with another are associated with complications related to bleeding, surgical adhesions, destruction of bone, and other generic risks associated with surgical procedures. Accordingly, improved devices that address these issues would be desirable.

A number of spinal deformities exist where the spine is abnormally twisted and or curved. Scoliosis is typically considered an abnormal lateral curvature of the vertebral column.

Correction of scoliosis has been attempted a number of ways. Typically correction is followed by fusion. A Harrington rod has been used where a compressing or distracting rod is attached above and below a curved arch of the deformity. The spine is stretched longitudinally to straighten the spine as the rod is lengthened. The spine is then fused. The correction force in this device and in similar devices is a distraction force that may have several drawbacks including possible spinal cord damage, as well as the high loading on the upper and lower attachment sites. Nowadays, segmental hook and screw fixation exists for distraction and derotation corrective forces.

A Luque device has been used where the spine is wired to a rod at multiple fixation points along the rod and pulls the spine to the rod. The spine is pulled to the rod with a wire and the spine is then fused. This does not provide significant adjustment over time and requires fusion. Once completed this does not provide an opportunity for delayed adjustment over time. Anterior procedures also exist in the form of fusion and newer technology involving staples across the disc space that obviate the need for fusion but still correct the deformity. The corrective force is derotation with or without compression.

Accordingly it would be desirable to provide an improved corrective device for treating scoliosis or other deformities. It would also be desirable to provide a device that may be used without fusion.

Spine surgeons commonly use metallic or polymeric implants to effect or augment the biomechanics of the spine. The implants frequently are attached or anchored to bone of the spine. Sites typically considered appropriate for boney attachment have high density or surface area, such as, for example, the pedicle bone, the vertebral body or the cortical bone of the lamina. The spinous process contains thin walls of cortical bone, and thus, has been considered as not ideal for anchoring spinal implants as they may not support the implants under physiologic loads, or the intermittent high loads seen in traumatic situations. Fixation has been attempted from spinous process to spinous process with poor results.

A translaminar facet screw as used by some surgeons goes through the base of spinous process to access the cancellous bone of the lamina. A disadvantage of this device is that it is not suitable for attaching to a pedicle screw and the depth and angle during deployment can be very difficult to track or visualize, thus increasing the possibility that the screw would extend into the spinal canal. A facet screw is screwed between opposing facets of a zygapophyseal joint.

SUMMARY OF THE INVENTION

One aspect of the present invention is directed to providing a device and method for alleviating discomfort and or deformity associated with the spinal column. Another aspect of the present invention is directed to providing a minimally invasive implant and method for alleviating discomfort associated with the spinal column. Another aspect of the present invention provides an anchoring device and method that requires less surrounding tissue damage or disruption. Another aspect of the present invention provides reinforcement of the spinous process for use in various spinal systems. Another aspect of the invention provides a minimally invasive, non-invasive, or remote adjustment or lengthening of an orthopedic device. Another aspect of the invention provides a minimally invasive, non-invasive, or remote adjustment, lengthening or shortening of a stabilization device. Another aspect of the present invention also provides an implant system and device suitable for minimally invasive, minimally disruptive and/or percutaneous posterior deployment across a plurality of motion segments and more than two motion segments. Different aspects of the invention may provide distraction forces to relieve pressure on certain structures, compression forces to fix or stabilize motion across structures, shock absorbing qualities to help relieve load from certain structures, and therapeutic activity to reduce inflammation and pain. Other aspects of the invention may supplement or bear load for degenerated, painful, or surgically removed joints, e.g., the facet joint. Another aspect of the invention may provide a method and system for treating deformities such as scoliosis. Other aspects of the invention may include sensors associated with implants or implanted at or near the bones, soft tissue, or joints of the spine and may provide feedback regarding the joint on an ongoing basis. The sensors may also be part of a feedback system that alters a property of an implant in response to sensing information. Another aspect of the invention may provide a device or method for delivering therapeutic substances at or near the spine.

In accordance with one aspect of the invention, a reinforcement structure is provided for supporting the spinous process and if desired, in addition, the lamina of a spine. The invention further provides a method and system for forming or implanting such structure in the spinous process or a region of cancellous bone in the lamina of a spine. The reinforcement system may include one or more systems of reinforcement and may be used before, during and/or after a spinal device (e.g. a stabilization, distraction or prosthetic device, etc.) is coupled to the spinous process.

Various aspects of the invention are set forth in the description and/or claims herein.

BRIEF DESCRIPTION OF THE DRAWINGS

FIG. 4B is a posterior lateral perspective view of a distraction system implanted in a spine in accordance with the invention.

DETAILED DESCRIPTION OF THE PREFERRED EMBODIMENT

Figure 1A:
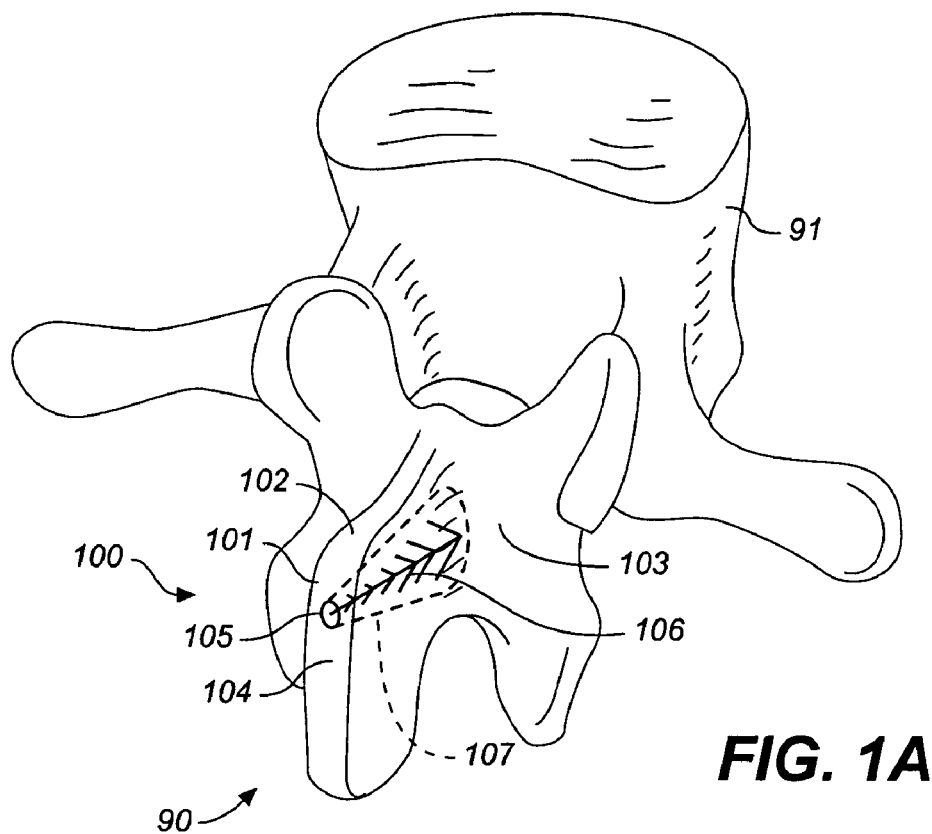
FIG. 1A is a lateral posterior view of a vertebra with a reinforcement structure in accordance with the invention.
Figure 1B:
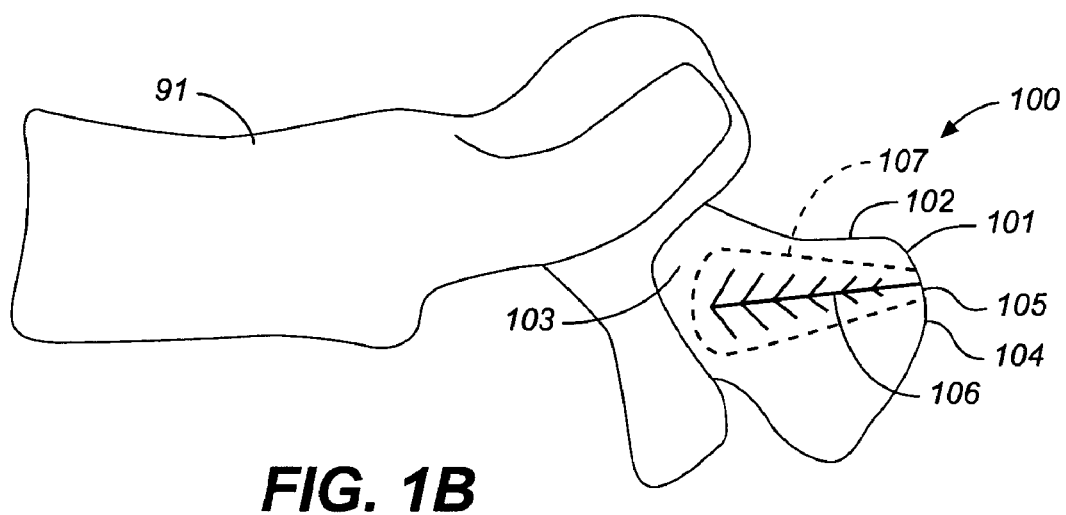
FIG. 1B is a side view of the vertebra and reinforcement structure of FIG. 1A.

FIGS. 1A and 1B illustrate a reinforced posterior arch 100 of a first vertebra 91 of a spine 90, including a spinous process 101 and lamina 103. The first vertebra 100 of the spine 90 as illustrated includes a first spinous process 101 with a superior portion 102 having a posterior ridge 104 into which a hole 105 is drilled. The hole 105 may be drilled with a drill, a trocar, a large bore IV needle or similar sharp object through the external and relatively hard cortical bone, to reach the internal cancellous bone within the spinous process 101 and adjacent the lamina 103.

Once the cancellous bone is accessed, optionally, a tool such as a balloon tamp, or other expandable member or small crushing or drilling member is used to create a cavity 107 or cavities within the cancellous bone by compressing, crushing or drilling out the bone material. X-rays may be used to determine how far to drill into the bone. The cavity 107 may be in the spinous process, through to the base of the spinous process, or through the spinous process and into the lamina. In one embodiment the cavity is cone shaped or widens as it moves anteriorly towards the lamina.

A reinforcing material is then delivered into the cancellous bone or cavity 107 of the spinous process 101 and/or within the lamina 103. The material is selected to provide reinforcing properties to the spinous process 101 and/or lamina 103 sufficient to support (whether alone or in combination with other support elements) a spine support structure, a prosthesis, or other device attached to the spinous process and or supported lamina. The material may be a bone cement or polymer with strength and hardness properties selected to provide sufficient reinforcement to the region so that the spinous process may be used at least in part, to support an implant structure for attaching to and manipulating the biomechanics of the spine. Examples include but are not limited to polymers such as acrylic cement developed for use in vertebroplasty procedures. The material may be a flowable polymer material that cures within the cavity. Suitable materials may be readily selected by one of ordinary skill in the art.

Reinforcement structures may be placed within the cavity prior to, during or after injection of flowable material for further strength properties. As illustrated, an additional support structure 106 is provided within the cavity. The support structure 106 may be inserted through a cannula and released to expand as a spring-like or self-expanding member, into the cavity. The support structure 106 provides further support of the spinous process and/or lamina. Alternatively, or additionally, one or more posts or struts may be provided within the cavity or extending out of the spinous process or lamina from the area of cancellous bone, to supplement the support of the spinous process or lamina in combination with the polymer or other curable material. The reinforcement structures may be formed of a number of different materials such as, e.g., a metal or biocompatible polymer. Such reinforcement structures may also be used in other bony areas of the spine including the vertebra, the pedicles, facets, the transverse process, etc.

Figure 2A:
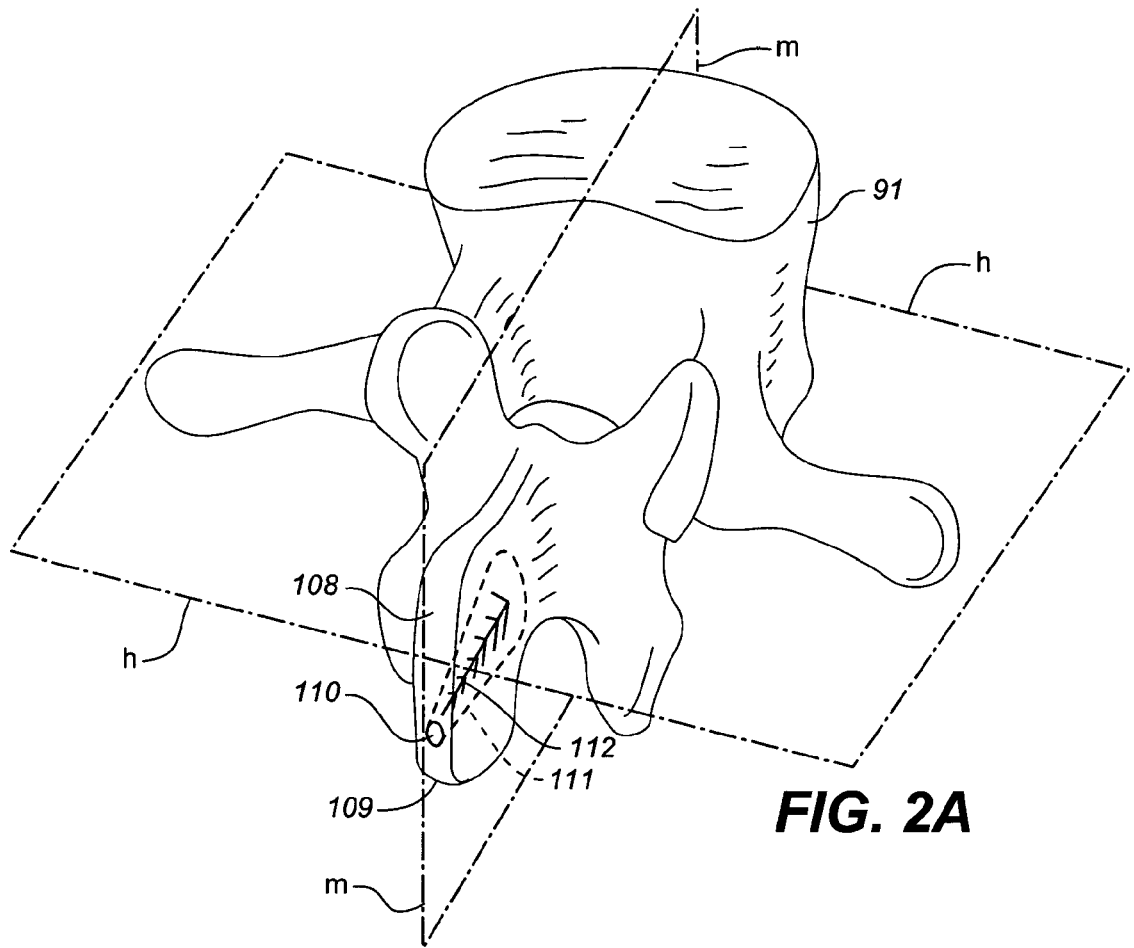
FIG. 2A is a lateral posterior view of a vertebra with a reinforcement structure in accordance with the invention.
Figure 2B:
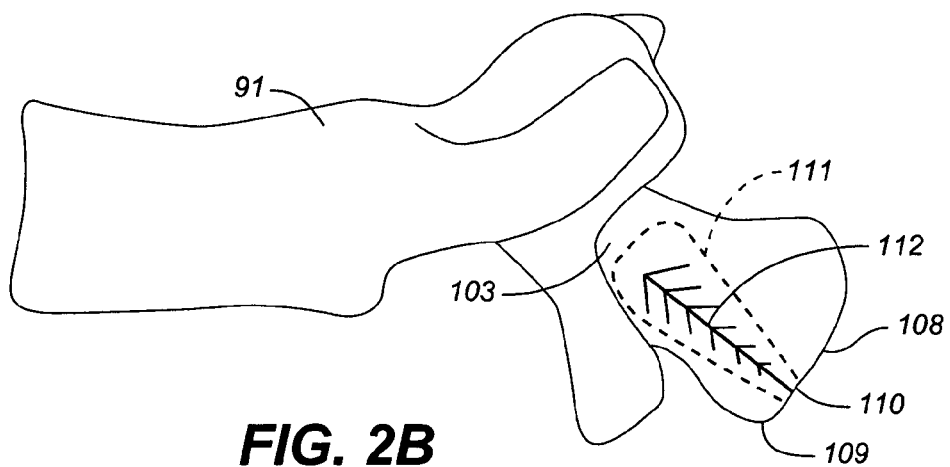
FIG. 2B is a side view of the vertebra and reinforcement structure of FIG. 2B.

As shown in FIGS. 2A and 2B, an inferior portion 109 of a spinous process 108 may also be reinforced. Similarly a hole 110 is drilled in the inferior portion of the spinous process 108 and a cavity 111 is formed. The cavity 111 is similarly filled with a curable polymer and is reinforced by reinforcing elements 112 positioned within the cavity.

The reinforcement structure may be used in a number of applications including increasing the strength of healthy bone to support the load and fixation of orthopedic implants, as well as increasing the strength of bone weakened by osteoporosis, chronic steroid use, avascular necrosis, weakened by injury and cancer involving the bone. According to one aspect, the reinforcement structure comprises a material that provides sufficient strength including but not limited to suitable polymers, e.g. PEAK, titanium, steel and carbon fiber.

The stabilizing and/or distracting devices described herein may be formed of a material that provides sufficient column strength including but not limited to suitable polymers, e.g. PEAK, titanium, steel, and carbon fiber.

Figure 3A:
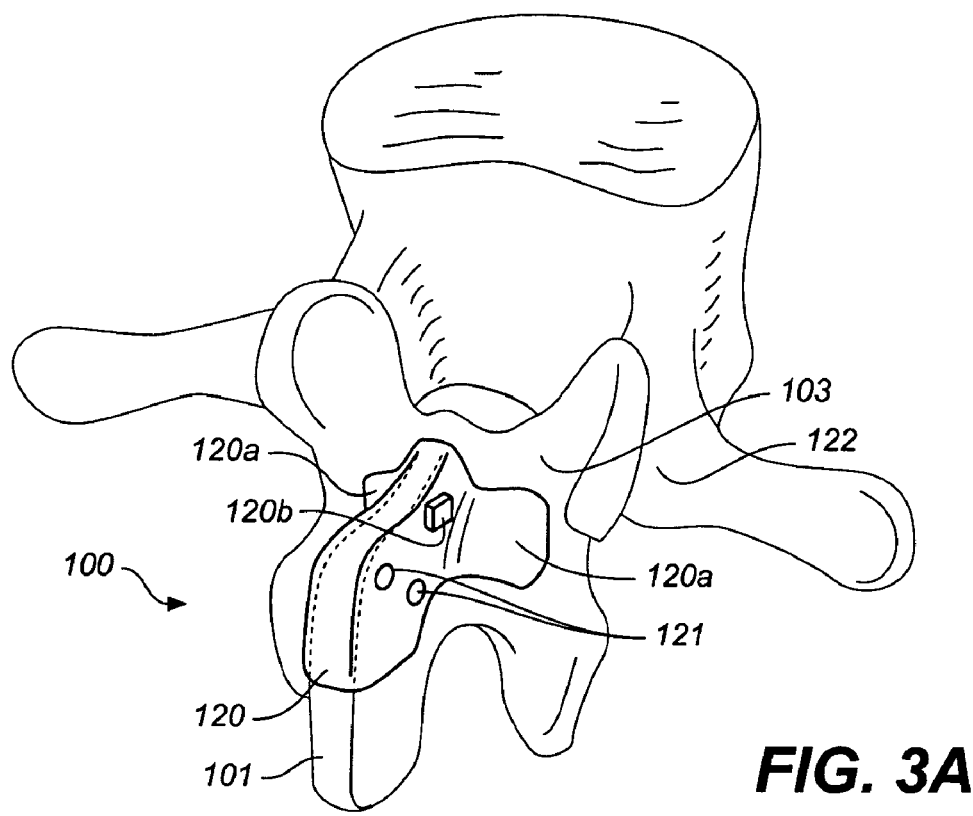
FIG. 3A is a lateral posterior view of a vertebra with a reinforcement structure in accordance with the invention.
Figure 3B:
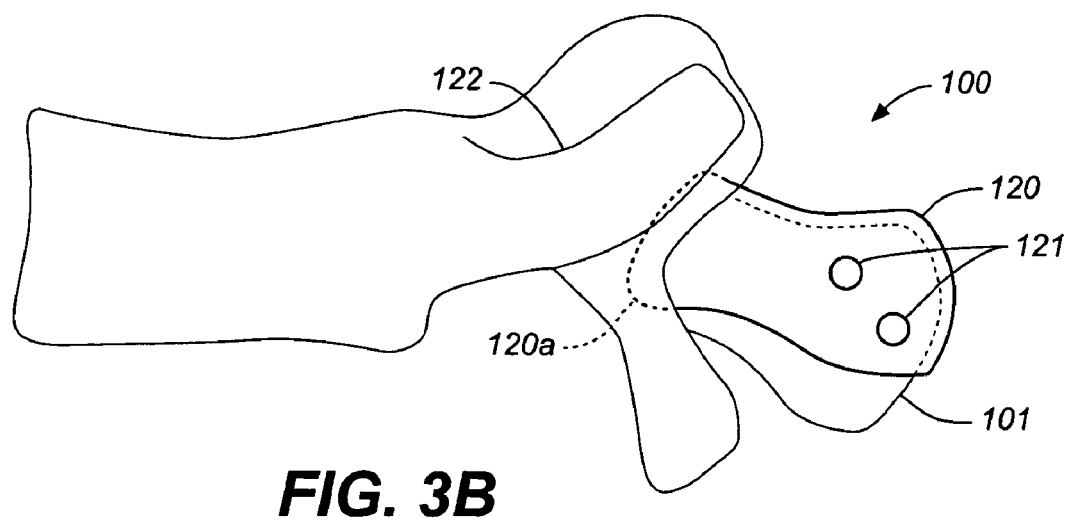
FIG. 3B is a side view of the vertebra and reinforcement structure of FIG. 3A.

Referring to FIGS. 3A and 3B, an alternative support structure 120 is illustrated. The support structure 120 allows the anchoring of implants under physiologic loads on the spinous process 101 while shielding underlying bone from loads that would normally cause the bone to fracture. (The implants may alternatively or in addition be anchored or attached to the lamina 103, e.g., with addition of small screws, barbs or adhesive that engage with the lamina while avoiding injuring the spinal cord surrounded by the lamina.) The support structure 120 comprises a hood like element positioned over the posterior arch 100, i.e., the spinous process 101 and lamina 103 of a spine 90. The support structure 120 may be made of a moldable or malleable material (e.g. putty, formable ceramic, clay-like material, or a moldable polymer or malleable alloy or metal) that cures into or forms a solid, strong structure. Heat, light, catalysts, precursors, or local pressure and force, for example, may be used to make the hood moldable or firm. The support structure of filling material to support the spinous process may be constructed or formed of moldable composites that can cure into hard material such as, e.g., ground glass powder or glass fiber fillers mixed into an acrylic matrix and activated with light or other biophysical modalities. Other cements or other curable materials may be suitable as well. The support structure 120 further comprises openings 121 to guide drill bits and/or for the placement of screws, reinforcement posts, or other instruments or supplemental support structures. The guide may insure accurate positioning of the implant. The support structure 120 may be anchored on the posterior arch by mold bending or forming the structure about the anatomy. The support structure 120 may be anchored into the lamina or spinous process by anchoring elements, such as, e.g., screws or barbs. The support structure 120 may also be anchored via screws or posts. Alternatively, the support structure 120 could be a preformed implant with contours that fit the anatomy of the posterior arch 100 or that are malleable or moldable to the anatomy. Also, the support structure 20 may be anchored into the pedicles 122 with screws, into the underlying bone with barbs, screws, bone anchors, or adhesives, over the edges of structures with hooks, or may be constructed of a plurality of pieces that may be assembled into one piece around the bone. Wings 120*a* of support structure may be placed over the lamina to spread the force of any device attached to the support structure 120

As illustrated in FIGS. 3A and 3B, a sensor 120*b* is positioned on the support structure 120. The sensor 120*b* may be embedded in the material. The sensor may sense stress on the support structure 120 from implants secured to it, or may sense other information that may be desirable to monitor. The sensor may include a communication element configured to communicate sensed information to an external device, e.g., when interrogated.

Figure 4A:
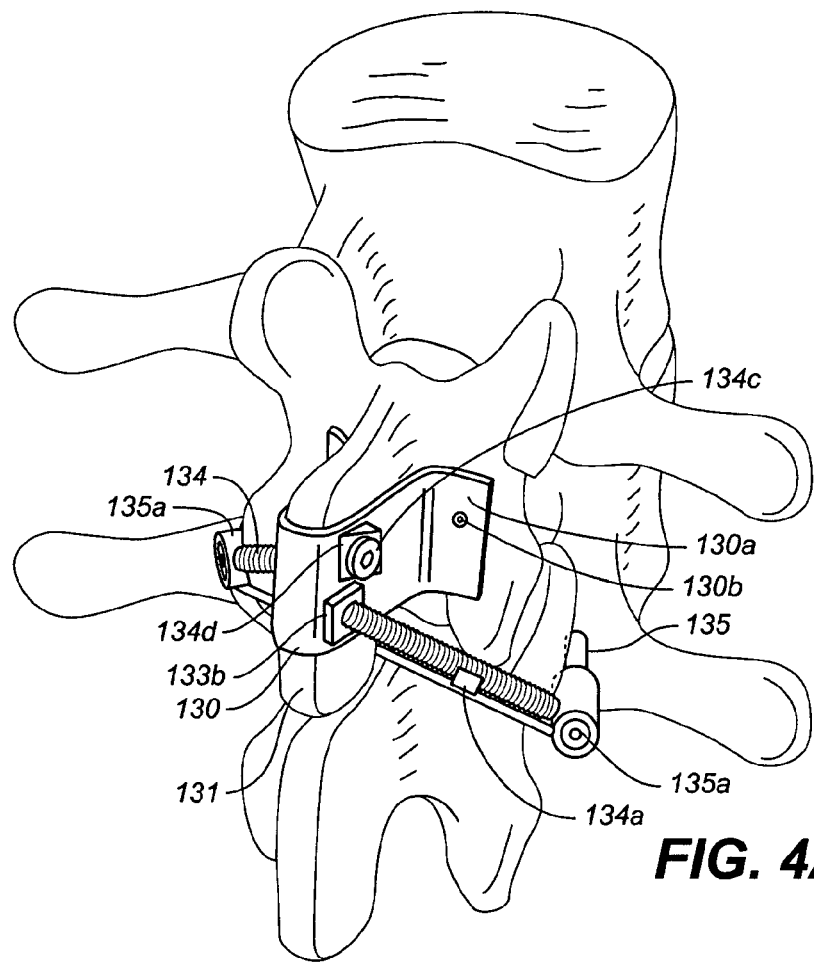
FIG. 4A is a lateral posterior view of vertebrae with a reinforcement structure and implant in accordance with the invention.
Figure 4B:
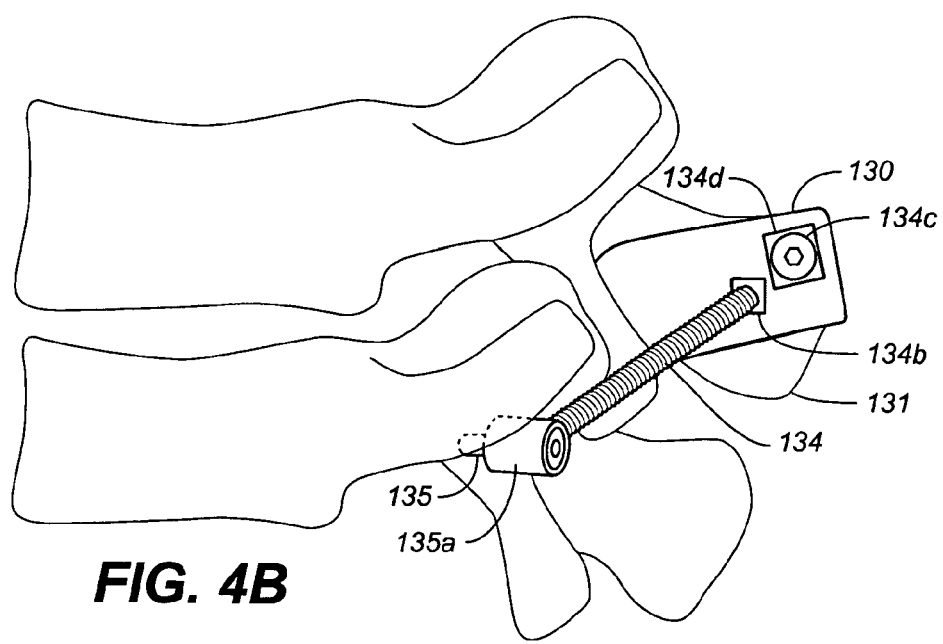
FIG. 4B is a side view of the reinforcement structure and implant of FIG. 4A.
Figure 4C:
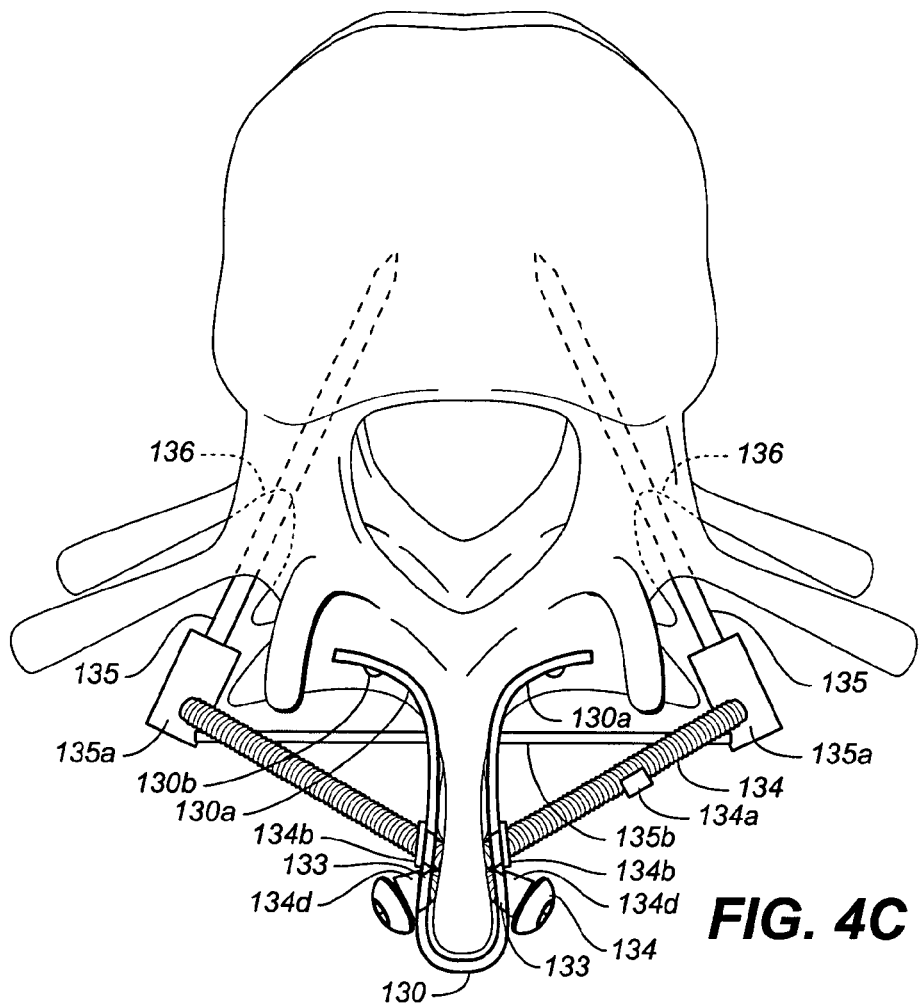
FIG. 4C is a top view of a reinforcement structure and implant in accordance with the invention.

Referring to FIGS. 4A-4D, a support structure 130 is illustrated positioned over a posterior portion 132 of a spinous process 131 with wings 130*a* over the lamina 103 including small screws 130*b* into lamina 103. Wings 130*a* may help spread the force from any devices attached or coupled to the support structure 130. Pedicle screws 135 are anchored into pedicles 136 and are further anchored into the spinous process 131 through screws 134 positioned through holes 133 in the support structure 130. As shown in FIG. 4C, the screw 134 includes a sensor 134*a* that may be used to sense loads on the device. Use of such sensors is described further herein. The pedicle screw 135 includes a screw capture device 135*a* for receiving a screw or rod of a spinous process screw or other rod. The capture device 135*a* may be a polyaxial head of a pedicle screw it may include a hole, a threaded screw hole with a washer or cap. Cross bar 135*b* is positioned across the spine between heads of pedicle screws 135 to prevent pedical screws from creeping laterally. A wedge shaped nut 134*d* between the head 134*c* of the screw 134 and the support structure. Another nut 134*b* may be positioned between support structure 120 and pedicle screw, and secure against the support structure 120. These features may be used in a similar manner in the embodiments described herein.

Figure 4D:
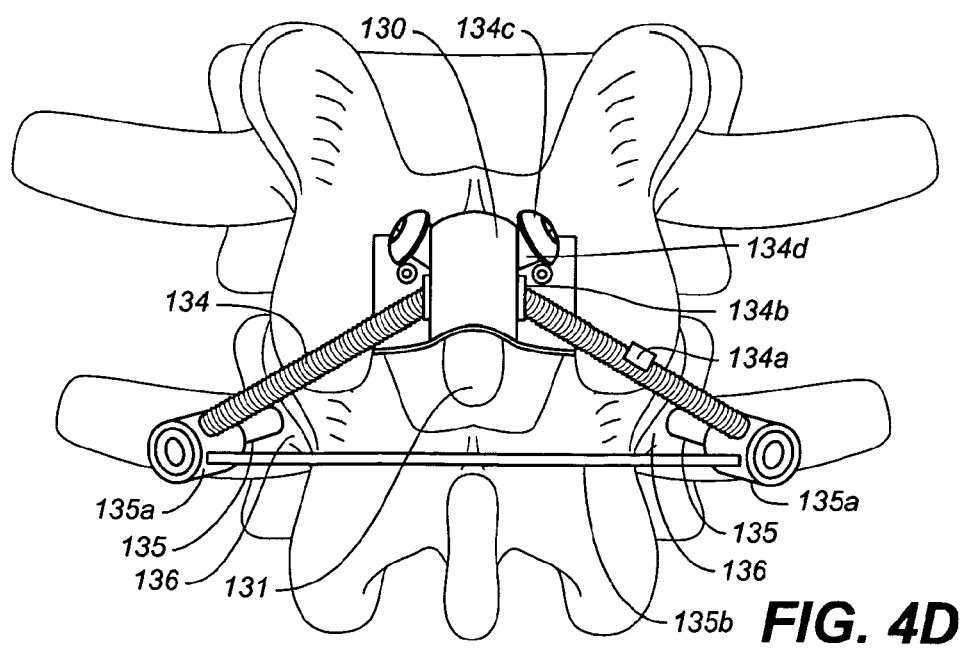
FIG. 4D is a posterior view of the reinforcement structure and implant of FIG. 4C.
Figure 5:
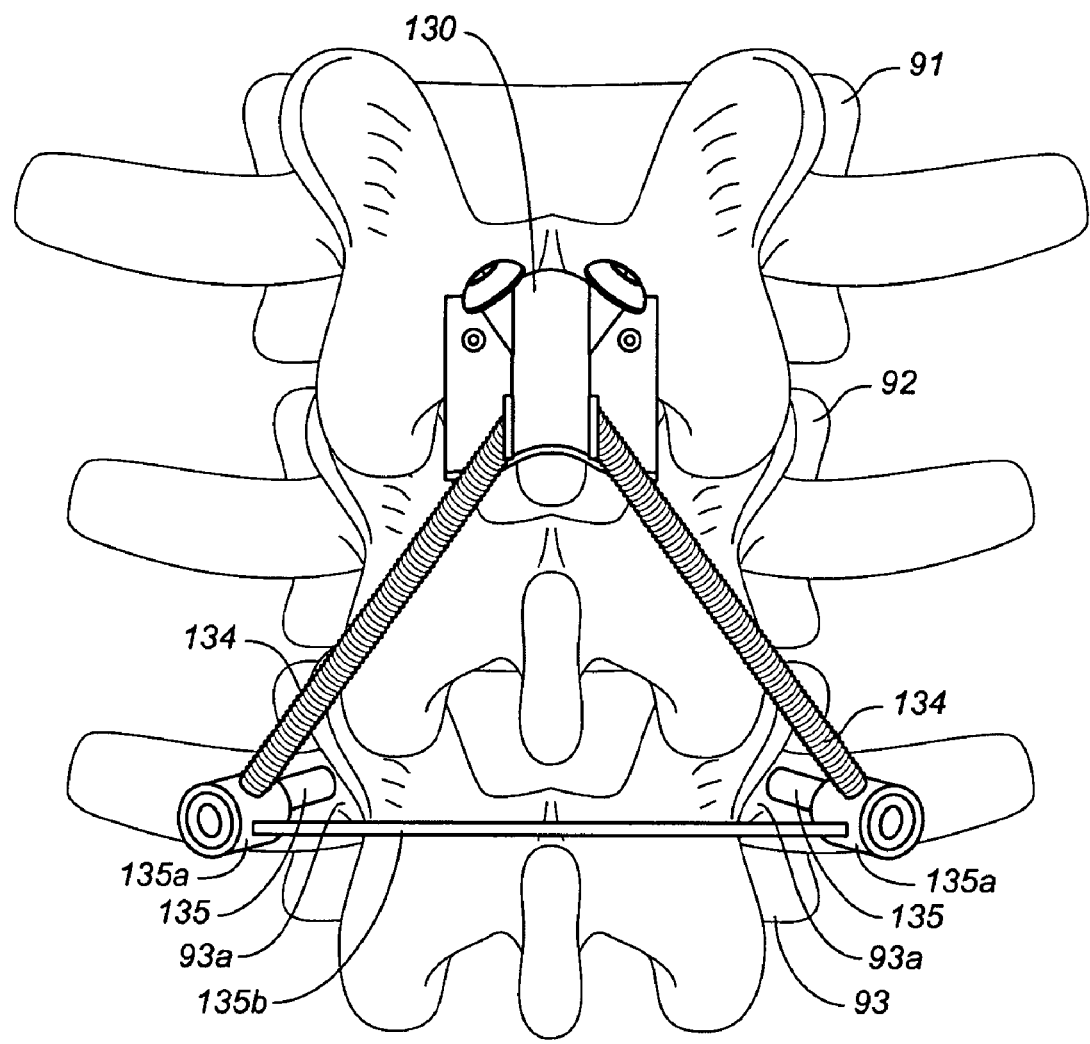
FIG. 5 is a posterior view of a reinforcement structure and implant in accordance with the invention.

FIG. 5 illustrates the spinous process screws 134 coupled to a spinous process 101 of a first vertebra 91 through a hood or support structure 130 in a manner similar to that described above with respect to FIGS. 4A-4D. The screws 134 extend bilaterally across the posterior of a second vertebra 92 and are anchored to capture elements 135*a* of pedicle screws 135 anchored into pedicles 93*a* of a third vertebra 93.

Figure 6:
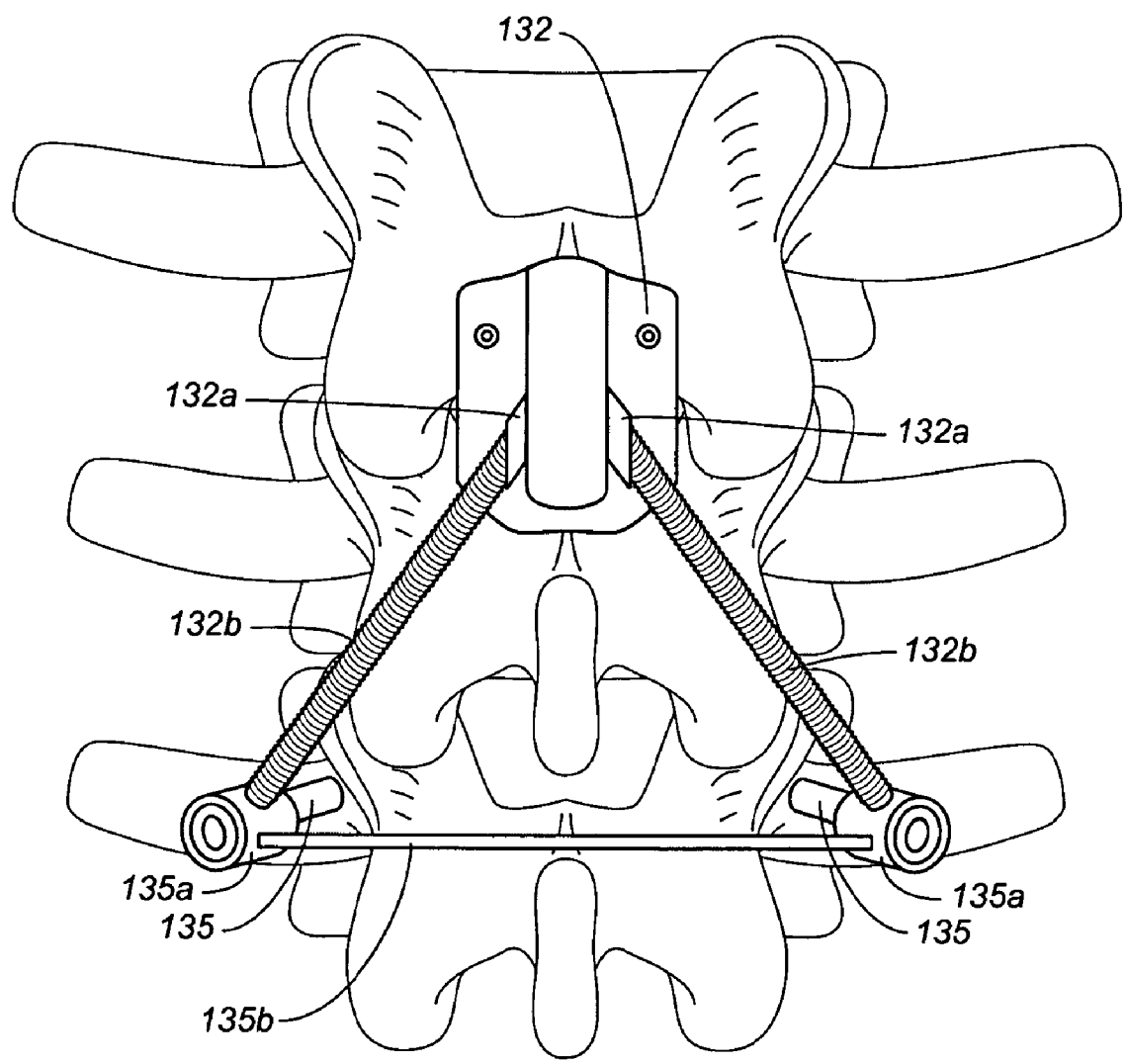
FIG. 6 is a posterior view of a reinforcement structure and implant in accordance with the invention

FIG. 6 illustrates a device for stabilizing or distracting the spine with pedicle screws 135 and cross bar 135*b* positioned as in FIG. 4D. Hood structure 132 includes openings for receiving screws 132*b* coupled to the hood 132 on one end and to the heads 135*a* of pedicle screws 135 and on the other end. The screws 132*b* do not penetrate the spinous process. Obliquely threaded nuts secure the screws 132*b* against the hood 132.

The reinforcement or supporting devices described herein may be used in conjunction with a number of different spine devices, including, for example, the various distraction, fusing or dynamic stabilizing devices described herein. The hoods or reinforcement devices herein may also be customized, for example by using stereolithography. The hoods or reinforcement devices may be used for example with a brace. The pedicle screw may be telescoping as described with respect to FIGS. 22C and 22D.

The devices described herein may be coupled to the spinous process using minimally invasive techniques. These techniques may include percutaneously accessing the spinous process and/or using dilators to access the spinous process at an oblique angle with respect to median plane m and/or horizontal plane h through the spine of the patient.

Figure 7A:
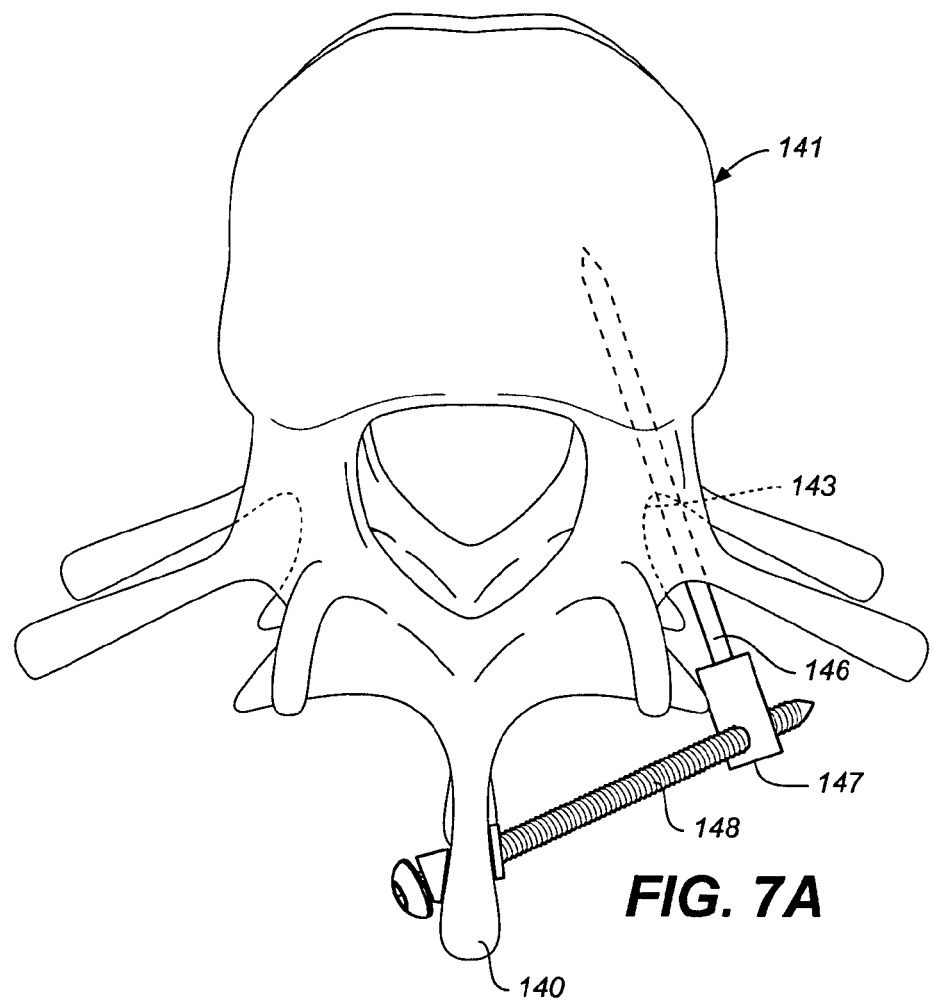
FIG. 7A is a top view of an implant implanted adjacent a motion segment in accordance with the invention.
Figure 7B:
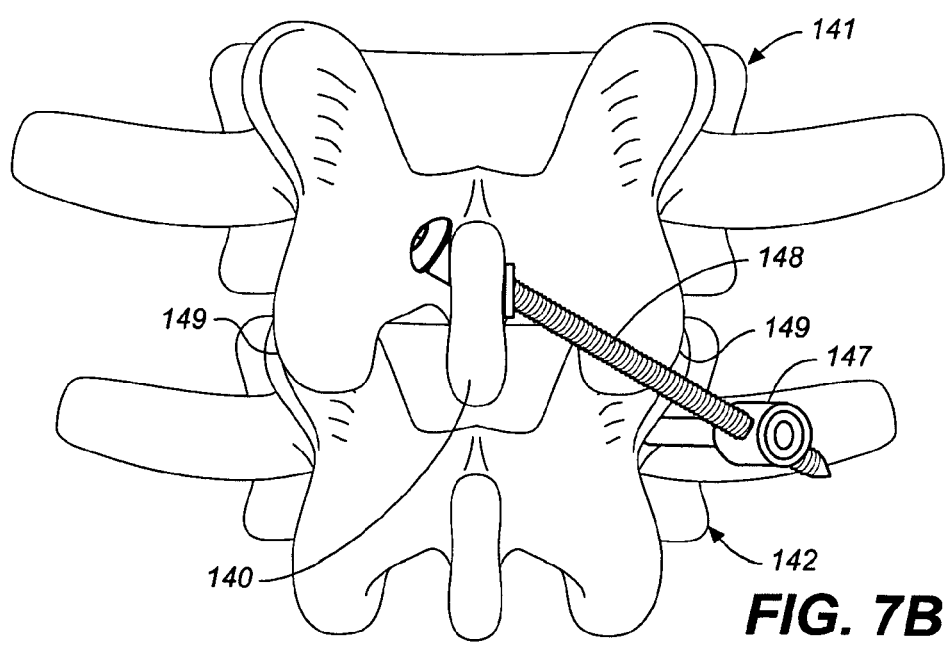
FIG. 7B is a posterior view of the implant as shown in FIG. 7A.

FIG. 7A is a side view of a joint of the spine with a fixation device percutaneously implanted to fuse adjacent vertebrae by fixation of the facet joints. Pedicle screw 146 in the pedicle 143 of the adjacent vertebral members 141, 142. As illustrated in FIG. 7B, the pedicle screw 146 has a polyaxial screw head 147 for receiving a spinous process screw 148 having a tapered tip. The spinous process screw 148 is screwed from the contralateral side of the spinous process, through the spinous process 140 of vertebral member 141, adjacent the facet joint 149 between the vertebral member 141 and vertebral member 142, and then captured or placed into the head 147 of the pedicle screw 146.

When implanted, the pedicle screws are positioned in the pedicles in a generally known manner. The facet joint or facet joints between the spinal members that are to be fused, are debrided and grafted. A flank stab wound is made to expose the base of the spinous process. The spinous process screw is then inserted and navigated through the wound to the spinous process and/or soft tissue. Tissue dilators or retractors may be used to facilitate insertion of the spinous process screw through soft tissue. The spinous process screw 148 is then placed through the spinous process 140, and into and captured by the head 147 of the pedicle screw 146. Compression across and the facet joint 149 may be provided using a nut placet in the polyaxial head of the pedicle screw. Alternatively, external compression may be used prior to placement of the oblique rod of the spinous process screw. A similar screw may also be placed from the spinous process 140 to the contralateral pedicle. The spinous process 140 may be reinforced prior to or after placing the screw 148.

Figure 8A:
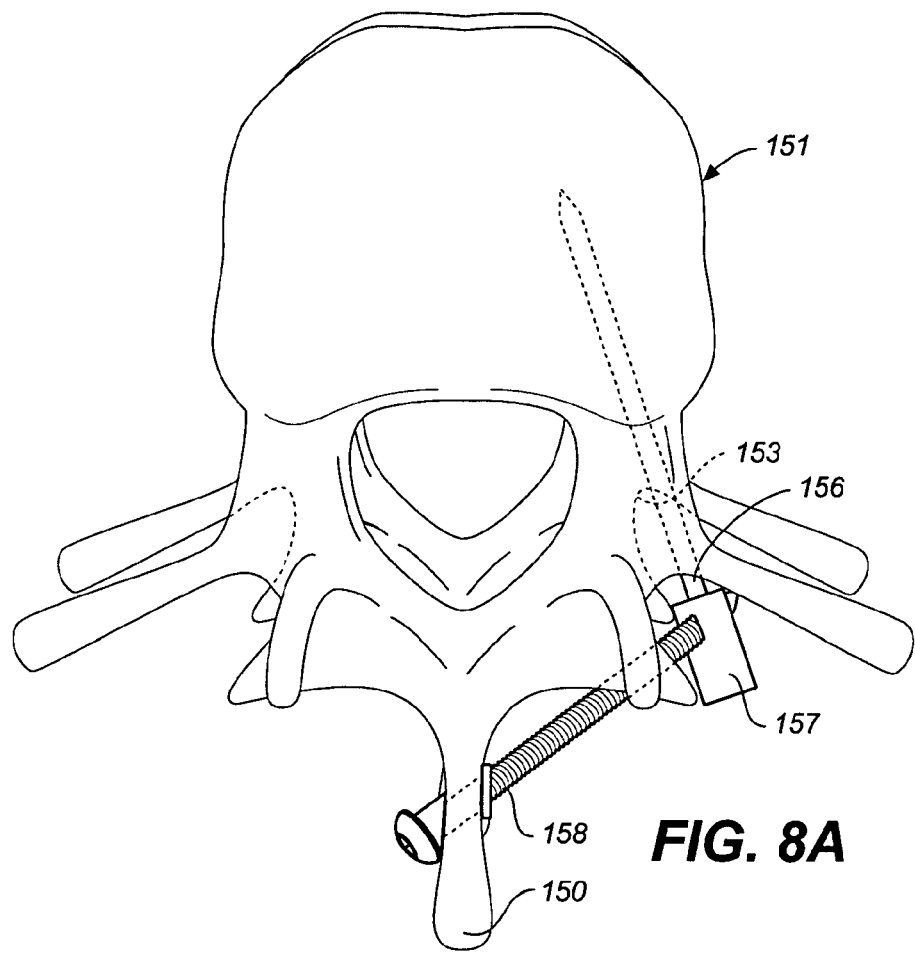
FIG. 8A is a top view of an implant implanted through the lamina and the zygapophyseal joint in accordance with the invention.
Figure 8B:
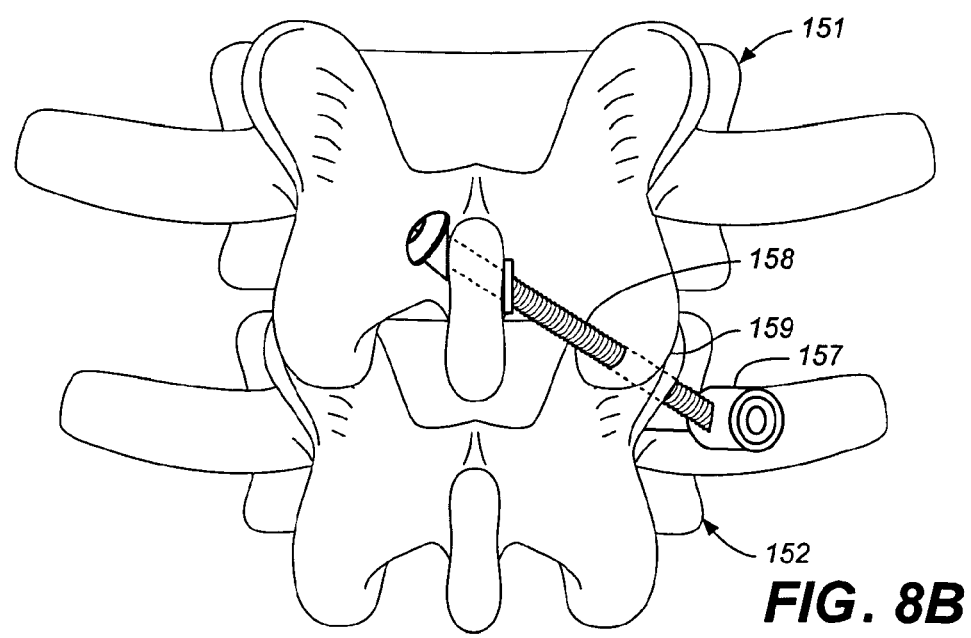
FIG. 8B is a posterior view of the implant as shown in FIG. 8A.

Referring to FIG. 8A, a similar fusion system as illustrated with respect to FIGS. 7A and 7B. Pedicle screw 156 is positioned in the pedicle 153 of the adjacent vertebral members 151, 152. The pedicle screw 156 has a polyaxial screw head 157 for receiving a spinous process screw 158 having a tapered tip. The spinous process screw 158 is screwed from the contralateral side of the spinous process 150, through the spinous process 150 of vertebral member 151, through the facet joint 159 between the vertebral member 151 and vertebral member 152 and then into the head 157 of the pedicle screw 156.

An oblique skin stab wound is made to navigate to the base of the spinous process 150, which may be exposed under direct vision. The spinous process screw 158 (or other device) is then placed through the spinous process 150, across (adjacent or through) the facet joint 159, and into the head 157 of the pedicle screw 156 (or otherwise attached to a pedicle attachment device for attaching devices to the pedicle), immobilizing the facet joint 159. A similar screw may also be placed from the spinous process 150 to the contralateral pedicle. The spinous process may be reinforced prior to or after placing the screw or other device. The other devices attached or coupled to the spinous process as described herein may be similarly deployed.

The devices described herein may be coupled to the spinous process using minimally invasive techniques. These techniques may include percutaneously accessing the spinous process and/or using dilators to access the spinous process at an oblique angle with respect to median plane and/or horizontal plane through the spine of the patient.

Figure 9A:
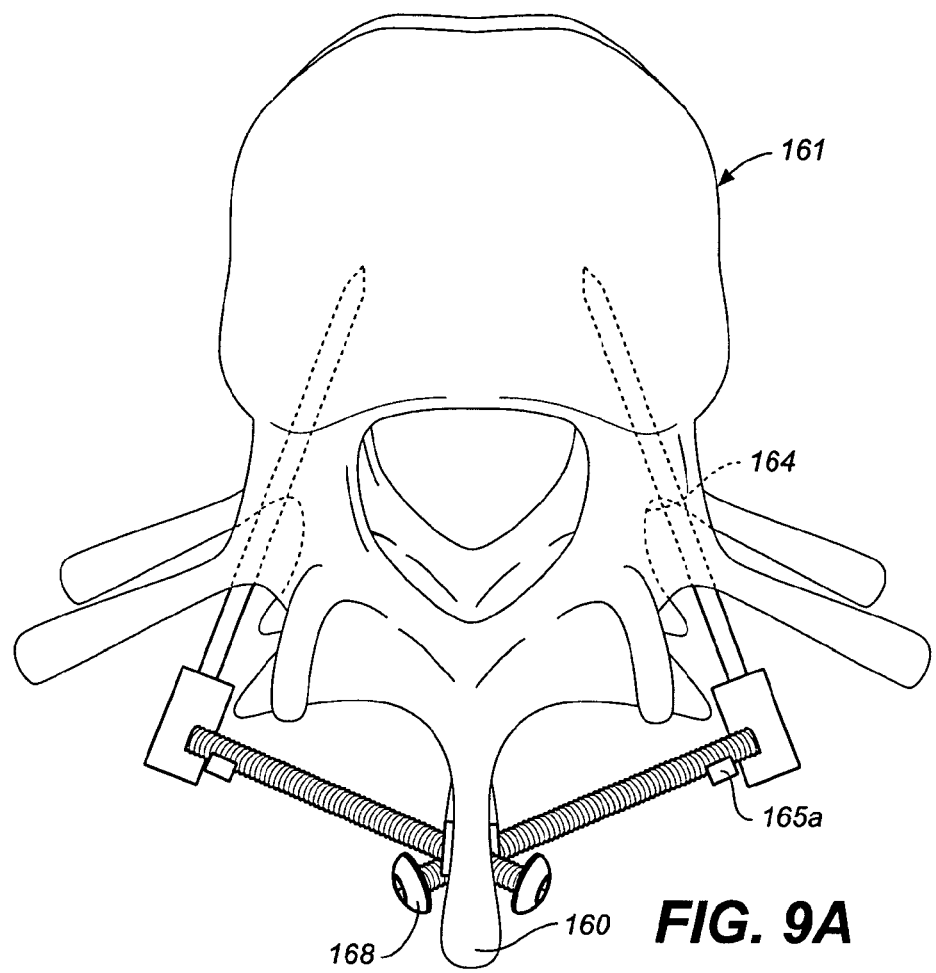
FIG. 9A is a top view of a dynamic implant in accordance with the invention.
Figure 9B:
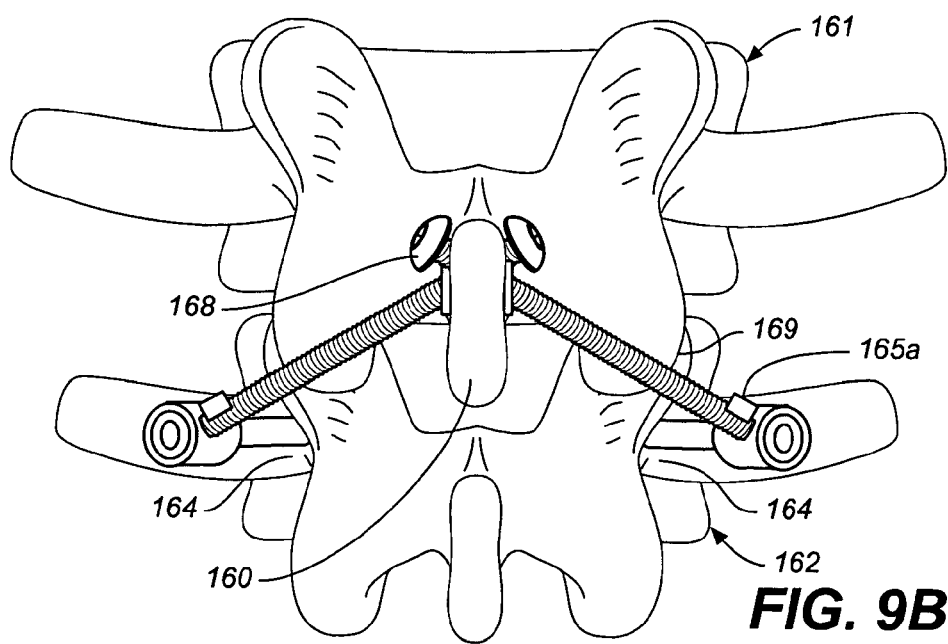
FIG. 9B is a posterior view of the implant as shown in FIG. 9A.

Referring to FIGS. 9A and 9B, a spine is illustrated with a spinal fusion system in place. A spinous process screw 168 is placed from the contralateral side of the spinous process 160, through the spinous process 160 of a first vertebra 161 and across the facet joint 169 between the first vertebra 161 and an adjacent second vertebra 162, and into the pedicle 164 of the second vertebra 162.

Another feature of the spinous process screw of FIGS. 9A-9B is that it may be configured to exert flexible, stabilizing, nonfusion forces to the motion segment. For example, this may be used in the event that patient suffers from pain due to laxity or other dysfunction of the spinal structures (e.g. degenerative spondylolisthesis). In other words, the looseness or other dysfunction of the joint and surrounding tissue may cause pain. The present invention provides a device and method for dynamically stabilizing (or reducing) such a joint while allowing some flexibility and movement. The device and method provide such stabilization on an oblique angle with respect to the rotational axis of the spine, i.e. at an oblique angle with respect to the median and horizontal planes of the spine. The spinous process and a pedicle could also be used to anchor a device exerting a stabilizing or compression or contractile force between the two anchors on an oblique angle. Devices that may be used to exert such a contractile force may include, for example, polymeric materials, super elastic metals, and fabrics. The spinous process screw 168 includes a sensor 165a that may be used to sense motion of the distraction device. The forces or stresses on the device may be monitored and used to determine if it is necessary to convert the device to a fusion type device or to otherwise reduce or alter motion. The sensor may also be used as a diagnostic device to measure the amount of joint motion upon insertion of the implant or over time.

The system illustrated in FIGS. 9A and 9B may also be used for the treatment of spondylolysis, to attain stability across the pars interarticularis.

The spinous processes 140, 150, 160 may be reinforced in a manner as described herein. The various rods or screws through the spinous processes 140, 150, 160 may also be positioned through a posterior arch reinforcing member as described herein.

Figure 10:
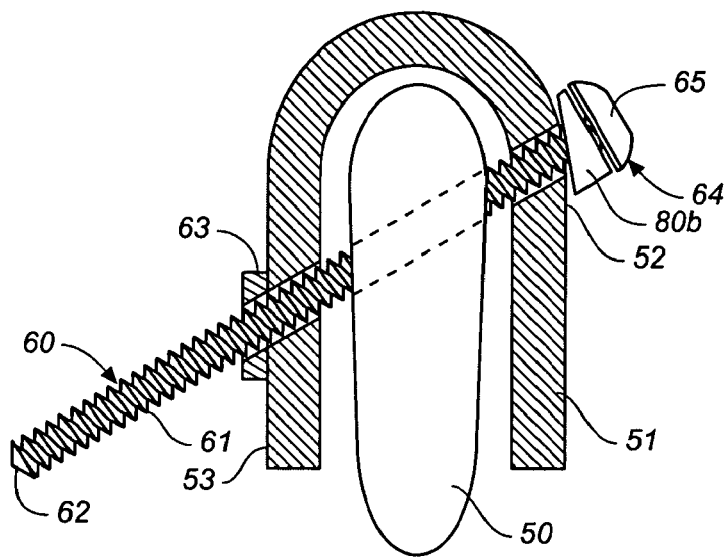
FIG. 10 is a schematic posterior portal cross sectional view of a reinforcement device and implant in accordance with the invention.

FIG. 10 illustrates a spinous process rod or screw 60 in accordance with the invention. The spinous process rod or screw 60 comprises an elongate portion 61 configured to extend through the reinforcement hood 51 (for example, as described in further detail herein with reference to FIGS. 3A-4D positioned around spinous process 50 and into an adjacent element such as, e.g. a pedicle screw. The spinous process rod or screw 60 may include threaded portions. The distal end 62 of the rod may be threaded or otherwise configured to engage an adjacent element. The spinous process screw or rod 60 further comprises a proximal securing element 65 located on the proximal portion 64 of the spinous process screw or rod 60. The proximal securing element 65 is configured to engage a first wall 52 portion of the spinous process 60 or reinforcement hood 51. ("Engage" as used herein means to either directly or indirectly engage.) As illustrated, the distal securing element 63 comprises an obliquely threaded nut that is configured to receive screw 61 which is coupled to the hood 51 at an oblique angle with respect to the wall 53. The oblique threaded nut may be used in other applications where a screw is oblique with respect to the abject to which is engaged, coupled or attached. The obliquely threaded nut may have a predetermined angle at which it directs the screw with respect to the hood to guide the desired angle or directions of the screw placement. This may be predetermined base on imaging of a particular patient's anatomy. A distal securing element 63 is provided more distal of the proximal securing element 65. The distal securing element is configured to engage a second wall portion 53 generally opposite the first wall portion 52 so that the spinous process element is secured or fixed to the hood and spinous process. (The term "fix" as used herein means either directly or indirectly fix to and may include dynamic elements.)

Figure 11:
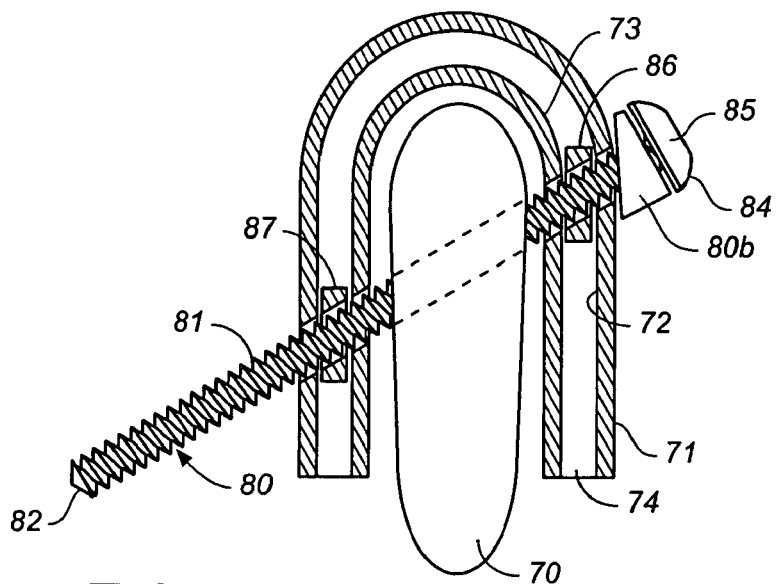
FIG. 11 is schematic posterior partial cross sectional view of a reinforcement device and implant in accordance with the invention.
Figure 12A:
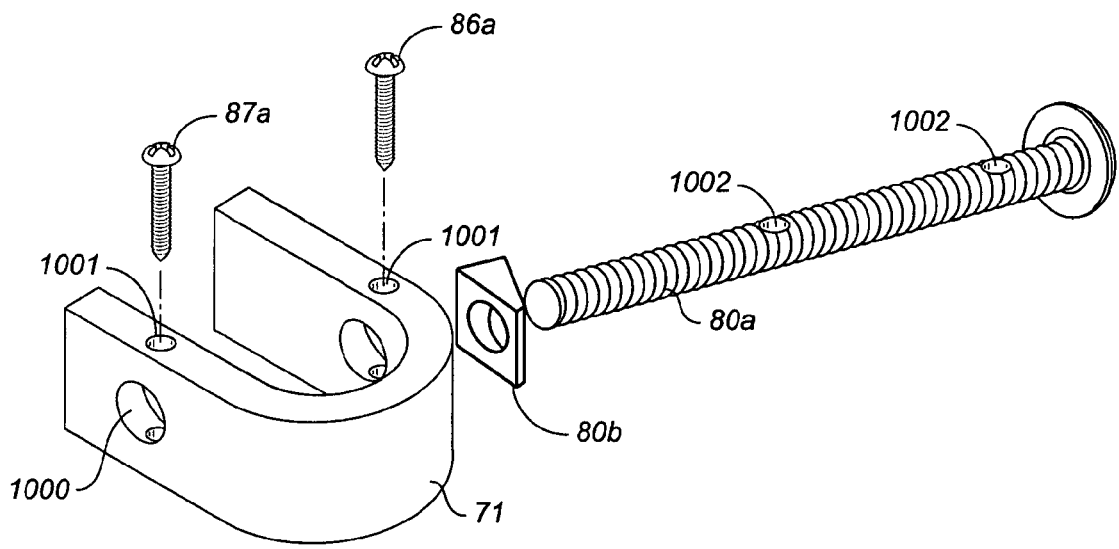
FIG. 12A is an exploded perspective view of a reinforcement device and implant in accordance with the invention.
Figure 12B:
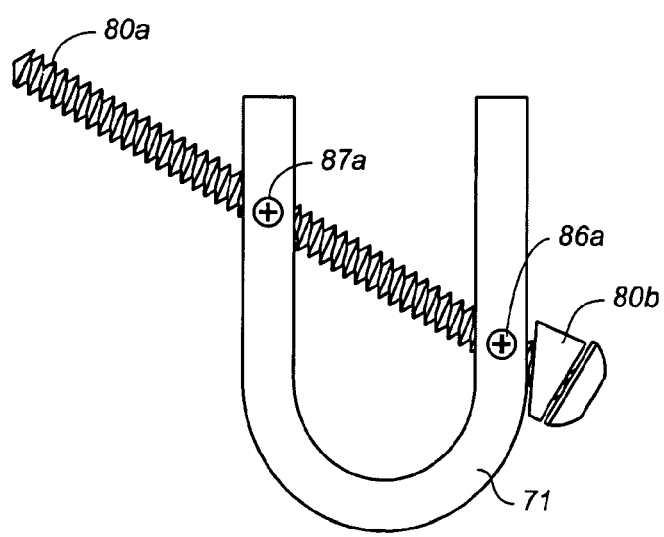
FIG. 12B is a top view of the reinforcement device and implant of FIG. 12A.
Figure 13A:
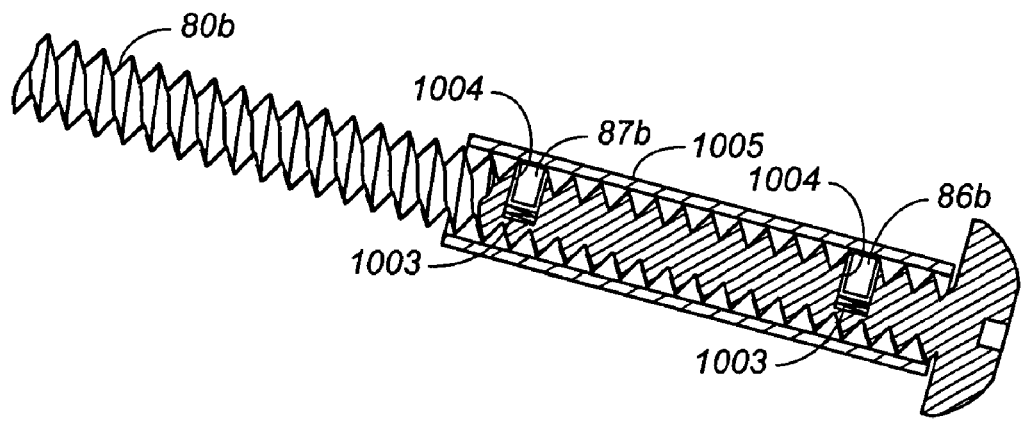
FIG. 13A is a schematic partial cross sectional view of an implant in accordance with the invention in a first position.
Figure 13B:
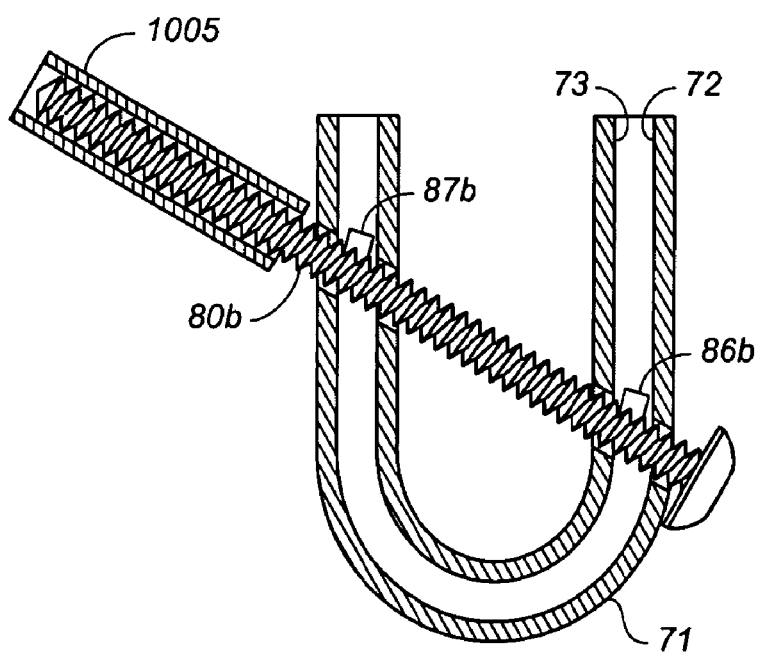
FIG. 13B is a schematic partial cross sectional view of the implant of FIG. 13A in a second, and implanted position.

FIG. 11 illustrates a spinous process rod or screw 80 in accordance with the invention. The spinous process rod or screw 80 comprises an elongate portion 81 configured to extend through the reinforcement hood 71 (for example, as described in further detail herein with reference to FIGS. 3A-4D) positioned around spinous process 70 and into an adjacent element such as, e.g. a pedicle screw. The spinous process rod or screw 80 may include threaded portions. The distal end 82 of the rod may be threaded or otherwise configured to engage an adjacent element, e.g. with a connecting member, including but not limited to connecting members described herein. The spinous process screw or rod 80 further comprises a proximal securing element 85 located on the proximal portion 84 of the spinous process screw or rod 80. The proximal securing element 85 is configured to engage a first wall 72 portion of the spinous process 70 or reinforcement hood 71. ("Engage" as is used herein to mean either directly or indirectly engage.) A hollow space or chamber 74 is formed in the reinforcement hood 71 so that the hollow chamber may engageably receive one or more securing elements, e.g. first and second securing elements 86, 87 therein. The securing elements 86, 87 may be positioned on either or both sides of the spinous process 70 through which the screw or rod 80 is positioned. As illustrated in FIG. 11, securing element 86 is positioned on the proximal portion 84 of the screw 80 while securing portion 87 is positioned on the distal portion 82 of the screw 80. Securing elements 86, 87 may be obliquely threaded nuts, for example, as described with respect to nut 80b in FIG. 3E. Securing elements may be attached a variety of ways, for example as illustrated in FIGS. 12A-12B and 13A-13B. FIGS. 12A-12B illustrate manual insertion of securing elements in accordance with the invention. Spinous process screw 80a is placed through both wings of the hood 71 while passing through holes 1000 as shown. Securing elements 86a and 87a are inserted into receiving holes 1001 within the hood 71 and receiving holes 1002 within the spinous process screw 80a. Securing elements 86a, 87a prevent movement of the spinous process screw 80a. FIGS. 13A-13B illustrate automatic deployment of securing elements in accordance with the invention. The securing elements 86b and 87b could be positioned in recesses 1004 in the spinous process screw 80b and spring loaded with springs 1003 attached inside of the recesses 1004. An external sheath 1005 is positioned around the spinous process screw 80b. The screw 80b is positioned through a spinous process and a hood. The securing elements are then deployed upon removal of an external sheath 1005. The securing element 86,86a, or 86b is configured to engage the first wall portion of the spinous process (or hood) from within the hood 71. The securing element 87, 87a, or 87b is configured to engage a second wall portion 73 generally opposite the first wall portion 72 so that the spinous process element is secured to the hood and spinous process.

Figure 14A:
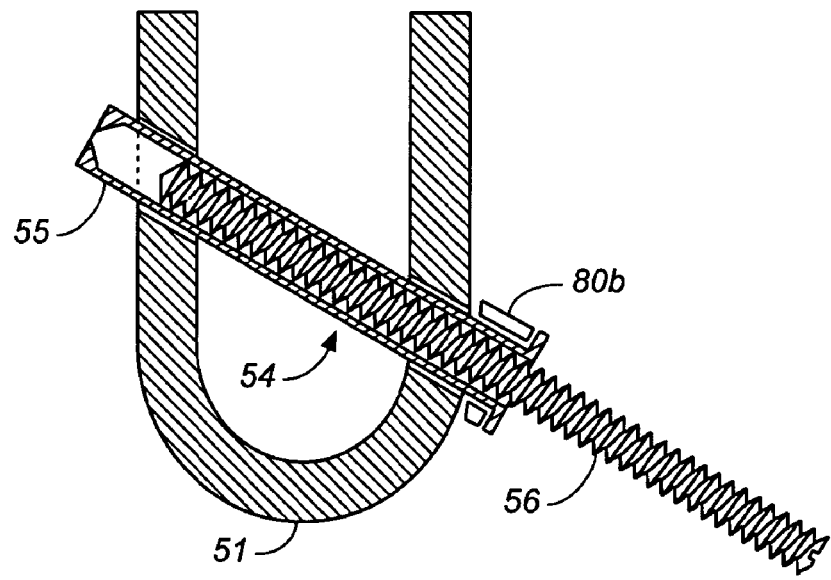
FIG. 14A is a schematic partial cross sectional view of an implant in accordance with the invention in a first position.
Figure 14B:
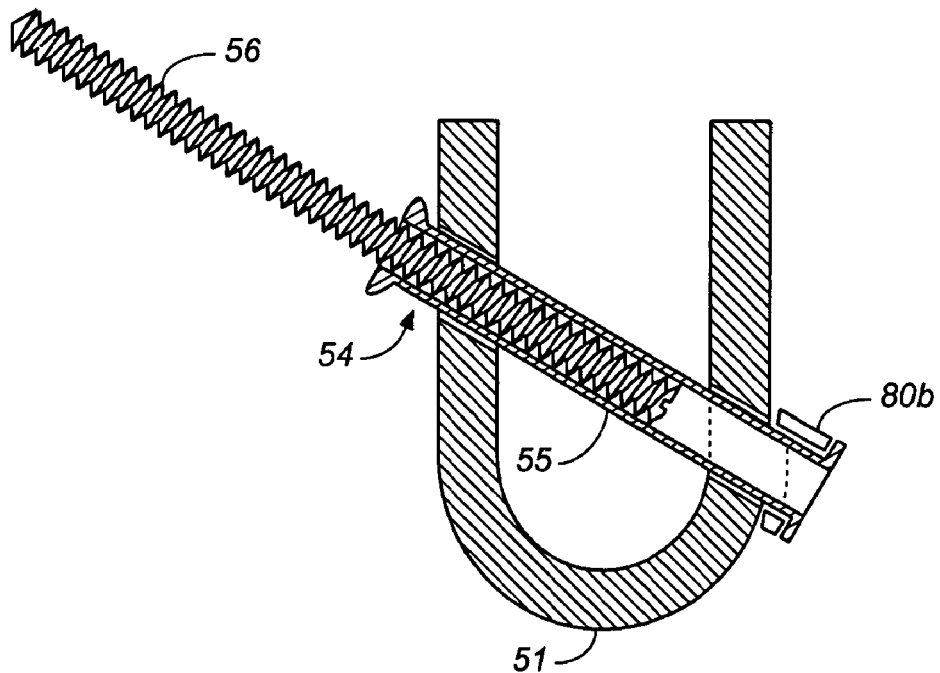
FIG. 14B is a schematic partial cross sectional view of the implant of FIG. 14A in a second position.

FIGS. 14A and 14B illustrate a spinous process rod or screw 54 in accordance with the invention. The spinous process rod or screw 54 comprises an elongate outer tube portion 55 and an inner rod portion 56. The inner rod portion 56 is configured to move longitudinally within the tube portion 55 to lengthen or shorten the spinous process screw or rod 54. The inner wall of the tube portion 55 may include a threaded inner wall that mates with a threaded outer wall of the rod 54 so that the rod may be screwed to advance the rod 56 and thereby lengthen or shorten the spinous process screw or rod 54. Once the outer rod 55 and screw 56 are positioned within a spinous process or hood 51 the spinous process screw or rod 54 may then be lengthened as shown in FIG. 14B to extend through the reinforcement hood 51. The lengthened spinous process screw may be used to distract the spinal segment or segments as well.

The pedicle attachment devices herein may include a sensor that may be used to sensor one or more parameters e.g., strain, pressure, motion, position change, that provides information about possible screw failure. The sensor may communicate the information to an external device, e.g. telemetrically, and may be passively powered by an external device.

According to another aspect of the invention a rod is provided that is anchored to with pedicle screws with screw heads made of or attached to swivel collars, polyaxial heads, or other movable fasteners to allow for near physiologic levels of motion of the spinal motion segment. Angular movement may be provided where a distracting element attaches on either side of a motion segment so that when distracting or lengthening the device, there is accommodation in the device for the change of angle that occurs.

Figure 15:
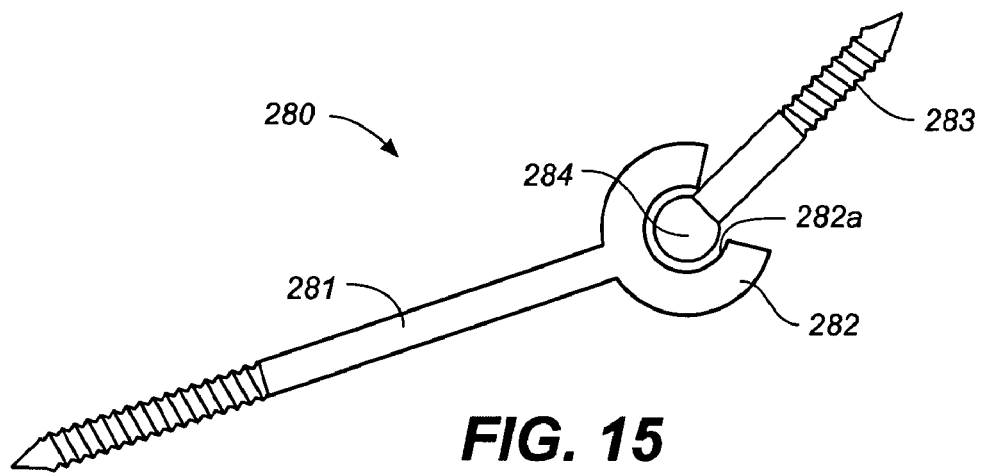
FIG. 15 is a schematic side view of a connector of an implant in accordance with the invention.

FIG. 15 illustrates an enlarged portion of a spinal prosthesis. The prosthesis 280 may provide support of the load on the spine where a facet has been removed or may provide other support or distraction. The prosthesis 280 comprises a distraction bar 281 used to distract a motion segment of the spine in a number of manners including the distraction devices described herein. A pedicle screw 283 is screwed into a pedicle of the spine or other anatomical location. The distraction bar 281 includes and articulating cup 282 having an inner surface 282a. The pedicle screw 283 has a ball 284 received by and coupled to the cup 282 of the distraction bar 281. In addition to shock absorbing capabilities described in various embodiments herein, the distraction bar 281 also articulates with a portion of the spine to which the pedicle screw 283 is attached.

Figure 16:
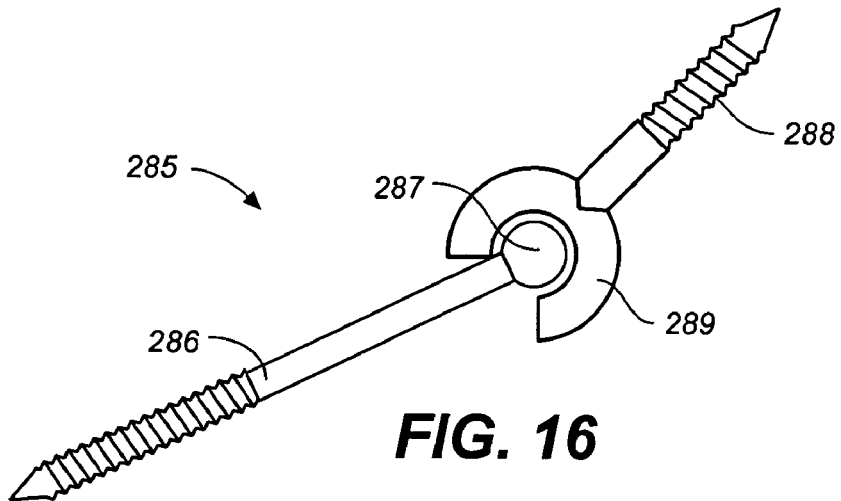
FIG. 16 is a schematic side view of a connector of an implant in accordance with the invention.

FIG. 16 illustrates a variation of the prosthesis 280 described with respect to FIG. 15. The prosthesis 285 comprises a distraction bar 286 and an articulating ball 287 configured to engage and couple with an articulation cup 289 of a pedicle screw 288. The prosthesis 285 operates in a similar manner as prosthesis 280.

Figure 17:
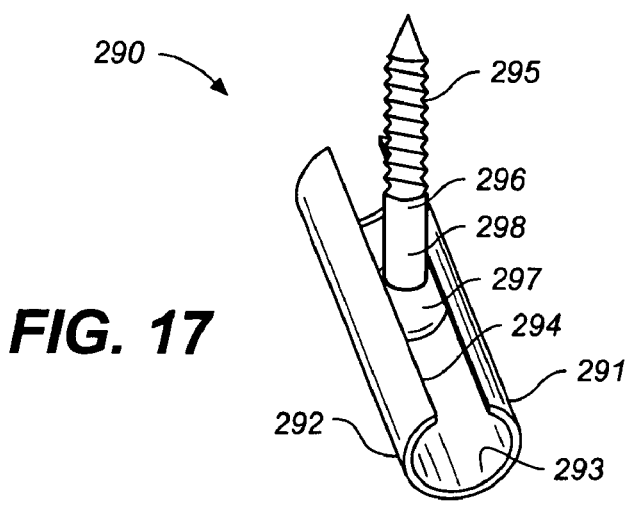
FIG. 17 is a schematic perspective view of a connector in accordance with the invention.

FIG. 17 illustrates a variation of the prostheses 280, 285 described herein respectively with respect to FIGS. 15 and 16. The prosthesis 290 comprises a distraction bar 291 having an end 292 with a lumen 293 for slidably receiving the end 296 of a pedicle screw 295. The end 296 of the pedicle screw 295 comprises a ball portion 297 attached to a neck 298. The ball 297 portion is configured to slide within the lumen 293 of the distraction bar 291 which contains the ball portion 297. The neck 298 of the pedicle screw 295 extends out of the distraction bar 291 through a longitudinal slit 294 that slidably receives the narrower neck portion 298 of the pedicle screw 295.

One embodiment of the invention is a rod anchored at each end across a motion segment that can be "switched" between dynamic stabilization and rigid fixation in a minimally invasive, percutaneous, or non-invasive fashion. One way for this to occur is injection of a flowable material within the lumen of the device, which would cure, and immobilize the components which allow for motion. Electrical current, heat, mechanical energy, or other techniques could also be used to render movable components fixed. Another method is insertion of a rigid implant axially along the length of the dynamic implant. This method of rendering a flexible prosthesis rigid may be applied to the design of other combination motion/fixation prostheses, including disc, facet hip, knee, fingers shoulder, elbows, and ankle prostheses, etc.

Figure 18:
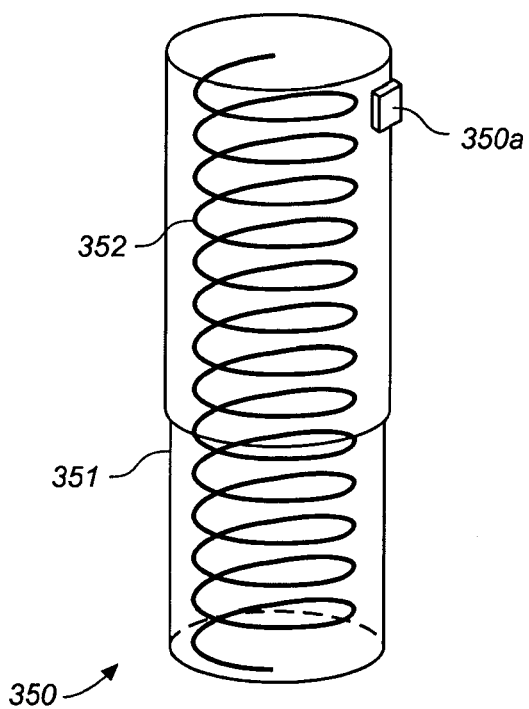
FIG. 18 is a schematic side perspective view of a dynamic element in accordance with the invention.
Figure 19:
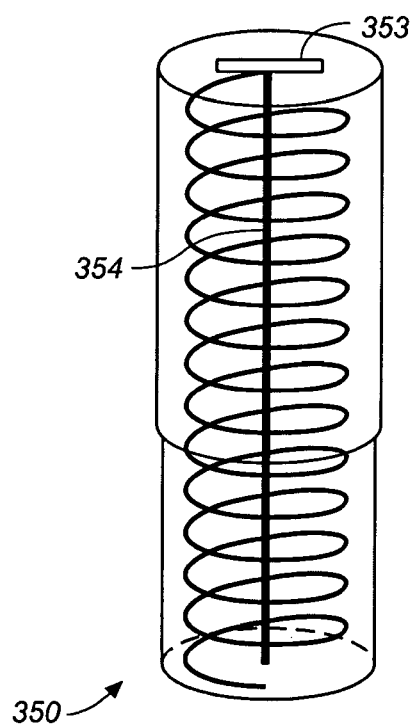
FIG. 19 is a schematic side perspective view of an adjustable implant element in accordance with the invention.

FIGS. 18-21 illustrate convertible or adjustable dynamic stabilization devices for joints. The stiffness or flexibility of the device may be altered or titrated after implantation to adapt the stiffness to a particular patient, and/or to adjust the stiffness over time, for example when laxity of the joint increases with age. Referring to FIG. 18 illustrates a dynamic stabilization prosthesis 350. The prosthesis comprises a flexible coil 352 contained in a tube member 351 comprising telescoping tubes. The prosthesis 350 may be used in a number of manners affixed across a joint motion segment to dynamically stabilize the joint. The coil 352 may be energy absorbing. The coil 352 may also be configured to exert a distracting force on the joint when implanted. FIG. 19 illustrates the dynamic stabilization prosthesis 350 of FIG. 18 converted to a rigid or more rigid prosthesis. The prosthesis 350 includes a slit 353 for receiving a rigid wire member 354. In FIG. 19 the rigid wire member 354 is inserted into the slit 353 to form the prosthesis from a dynamic prosthesis into a rigid prosthesis. As an alternative to a rigid wire member, a flexible coil of a selected stiffness may be inserted to change the stiffness of the dynamic prosthesis. The tube may alternatively comprise a ferromagnetic material contained therein and an electromagnetic field is applied that causes the prosthesis to become stiffer. The field may be varied to provide a variety of gradients in stiffness. The device may also include a sensor that operates as sensor 170a described herein. Feedback may be provided and the stiffness of the prosthesis adjusted accordingly. The stiffness may be varied when implanted using patient feedback so that the implant is more or less flexible depending upon an individual patient's needs. In addition the stiffness may be changed at different times during the course of the implants lifetime. For example, the stiffness may be increased when an increased amount of stabilization is required.

Figure 20:
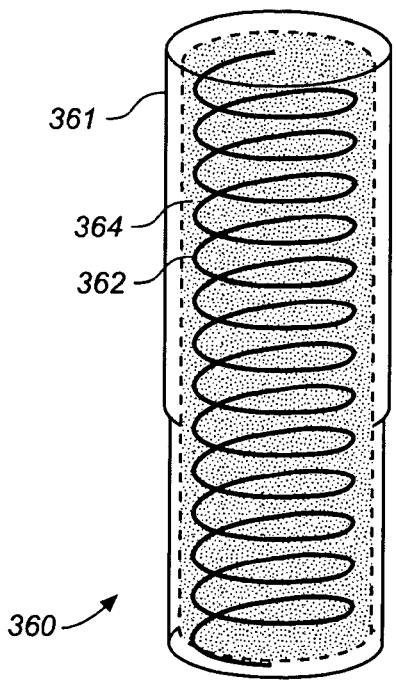
FIG. 20 is a schematic side perspective view of an adjustable implant element in accordance with the invention.

FIG. 20 illustrates an alternative prosthesis 360 also comprising a flexible coil 362 contained in a tube member 361. The tube member is configured to receive a fluid material such as a curable polymer 364 that cures in the tubular member to create a rigid prosthesis. As illustrated in FIG. 20 a rigid prosthesis is formed from a dynamic prosthesis by injecting the polymer material 364 into the tubular member 361. The flexibility/stiffness properties of the prosthesis may be selected by selecting such properties of the polymer to be injected.

Figure 21:
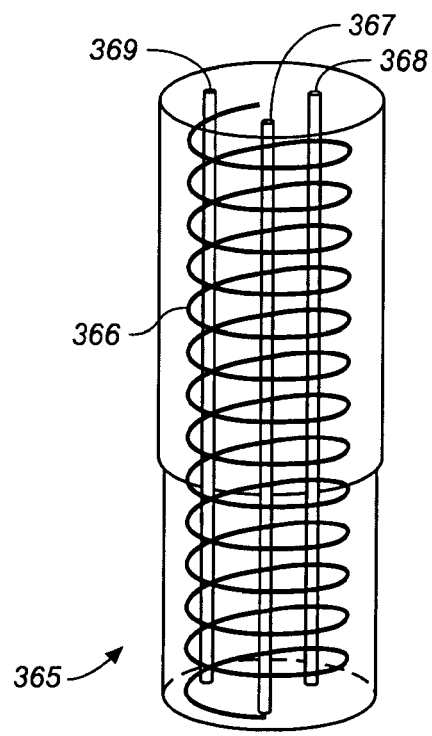
FIG. 21 is a schematic side perspective view of an adjustable implant element in accordance with the invention.

As illustrated in FIG. 21 a flexible prosthesis 365 is illustrated. The flexibility of the prosthesis 365 is adjustable by injecting a polymer material into one or more of the columnar cavities 367, 368, 369. The polymer may be injected into each cavity at a different time so the stiffness of the prosthesis may be increased gradually over time. The stiffness/flexibility properties of the polymer injected may also be selected according to a desired stiffness/flexibility of the implant.

According to an embodiment of the invention, the dynamic stabilizer may comprise a shock absorber that has both energy absorbing and energy dissipating properties. The tension band effect of the posterior columns may also offload the pressures borne by anterior column of the spine. So in addition to helping to protect the facet joints, other aspects of the invention would help slow the progression of degenerative disc disease, annular degradation, disc herniation, and vertebral compression fractures.

Another aspect of the invention is to supplement implants or repair procedures of the anterior column with a posterior shock absorber device (rod, screw, plate). Examples of these implants or procedures include total disc replacements, annular repair, artificial nucleus, and vertebroplasty/kyphoplasty.

Another aspect of the invention is to supplement implants or repair procedures of the posterior column with a shock absorber rod. Examples of these implants or procedures include interspinous distraction wedges, facet joint replacements, and posterior arch replacements.

Another aspect of the invention provides a posterior support implants with shock absorbing properties, to decrease or remove the load experienced by the facets. Implant components may include springs, coils, hydraulic or fluid filled piston chambers, or elastic materials. Each end of the device could be anchored in such a fashion so the rod bridges the facet joint, reducing the loads borne by the joint. This is believed to reduce wear of the facets and resulting pain and altered spinal biomechanics An improved device is provided that utilizes the spinous process, the pedicle, adjacent ribs and/or a transverse process or a combination including one or more of these anatomical structures, to correct or stabilize a deformed spine. The device may be used to correct scoliosis using one or more of these anatomical structures and multiple points at a plurality of spine segments. The correction may be made incrementally over time and may or may not include a fusion process.

In one embodiment, a percutaneously and obliquely placed rigid or dynamic stabilizer is provided. Stabilizer segments are anchored to base of spinous process at one end and a pedicle screw at the other end, as a unilateral temporary stabilizer. The dynamic stabilizers described herein may be adjusted over time to gradually bring the spine in alignment. The stabilizer may be used to derotate (untorque) and correct the spine. A stabilizer placed across a motion segment, i.e., not at the same vertebral level may be used to create overgrowth where desired, i.e. on the non-instrumented side of the motion segment. Such overgrowth may help stabilization or correction of the spine.

FIGS. 22A-24 illustrate an explantable, temporary scoliosis stabilization device. The system is configured to be manipulable once it is installed. The systems illustrated are configured to alter the orientation of a vertebral body and in particular to untorque the spine about the axis of the spinal column as well as applying a corrective straightening or translation force with respect to a vertical rod. According to one aspect of the invention, a device for correcting deformities of the spine is provided where the device may be adjusted over time to direct the corrective forces as needed over time. According to another aspect, a multipoint stabilizing device is coupled to the posterior portions of the spine.

Figure 22A:
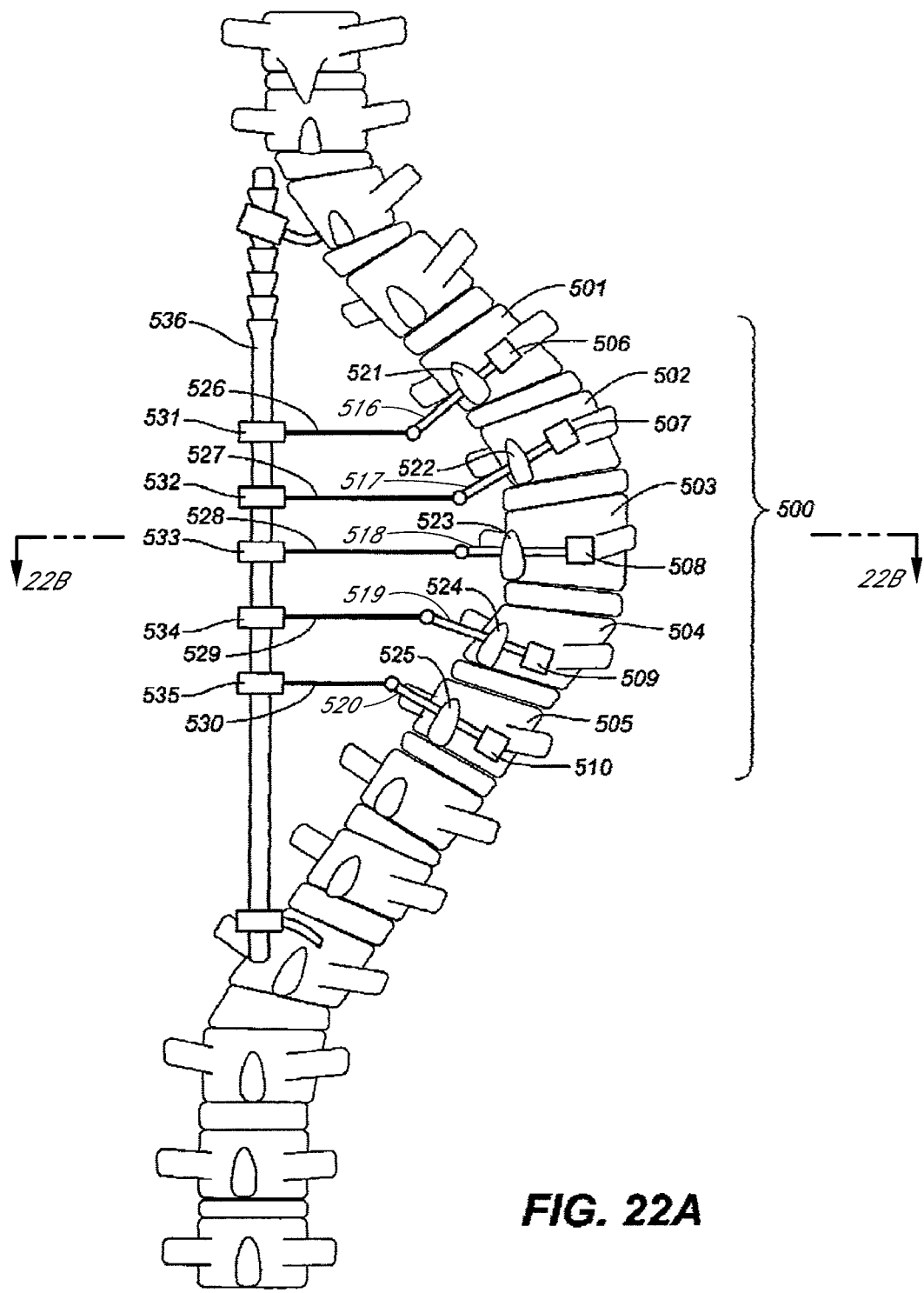
FIG. 22A is a schematic view of a spine deformity correction device in accordance with the invention.
Figure 22B:
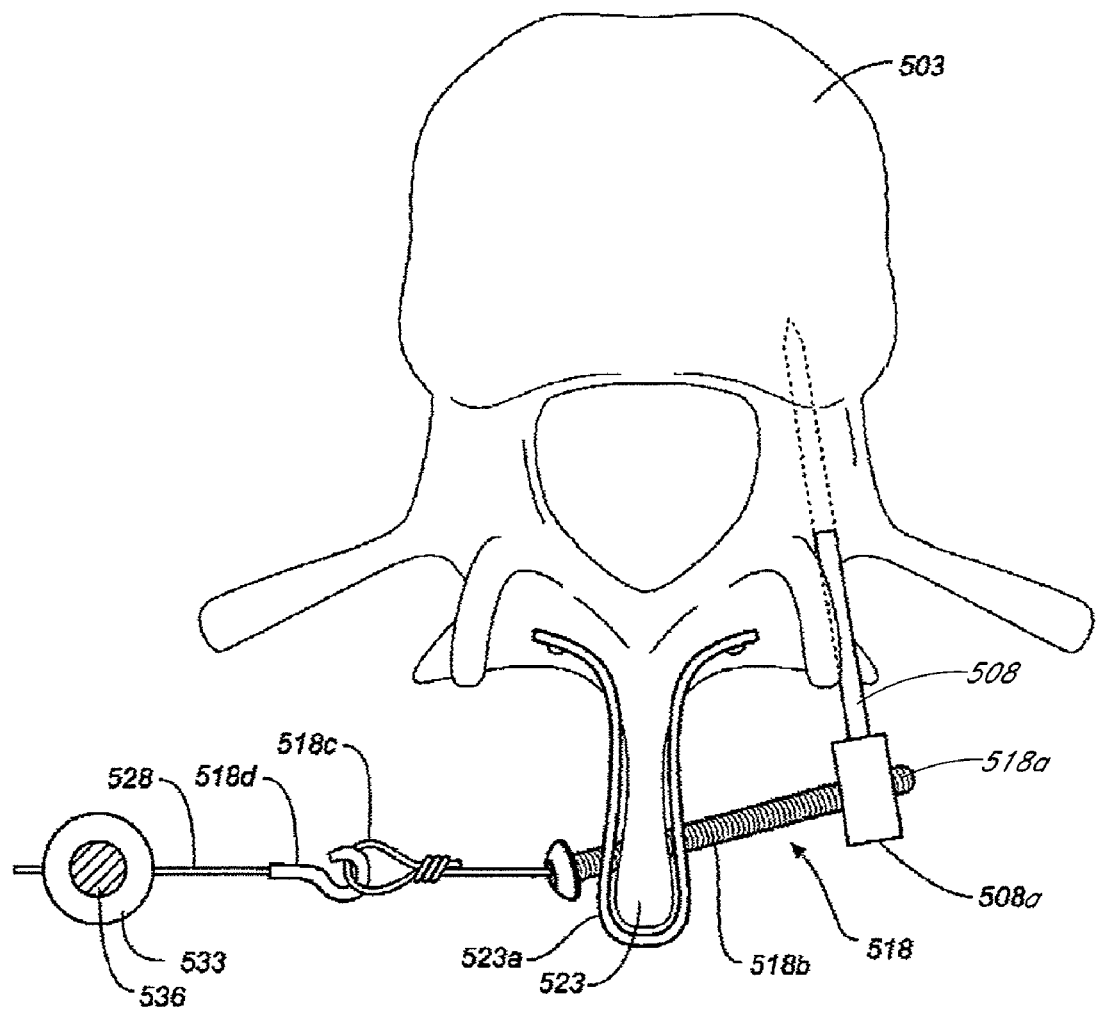
FIG. 22B is a cross section of FIG. 22A along the lines 22B-22B.
Figure 22C:
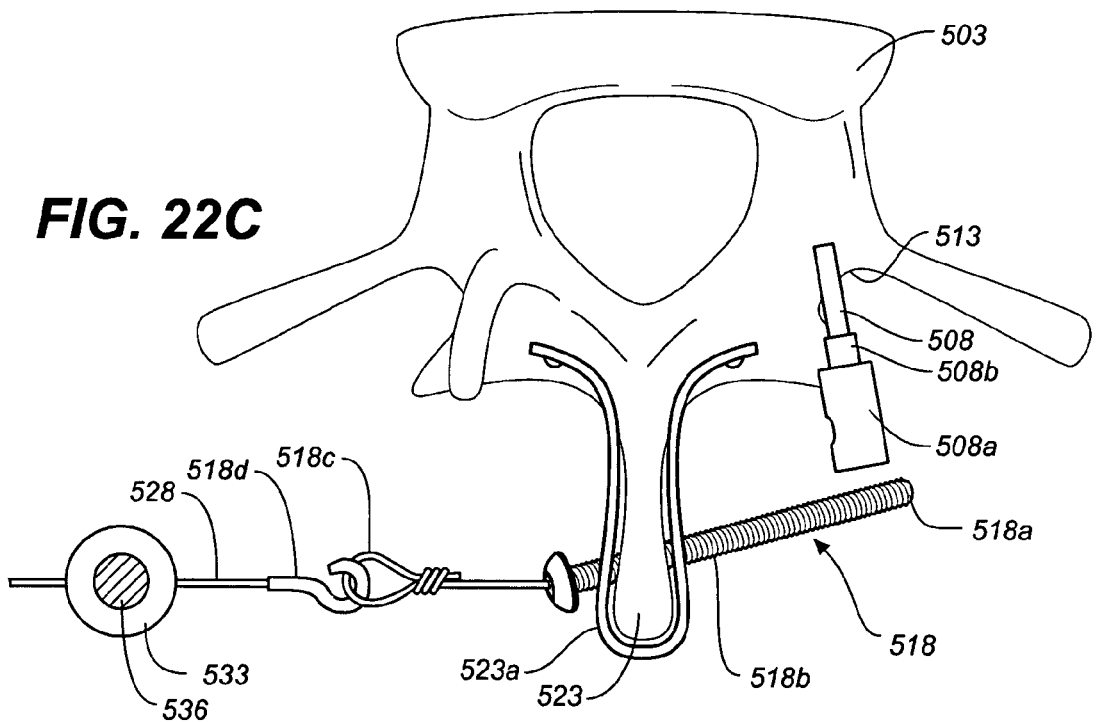
FIG. 22C is a schematic view of an adjustable pedicle attachment device in a first position in accordance with the invention.
Figure 22D:
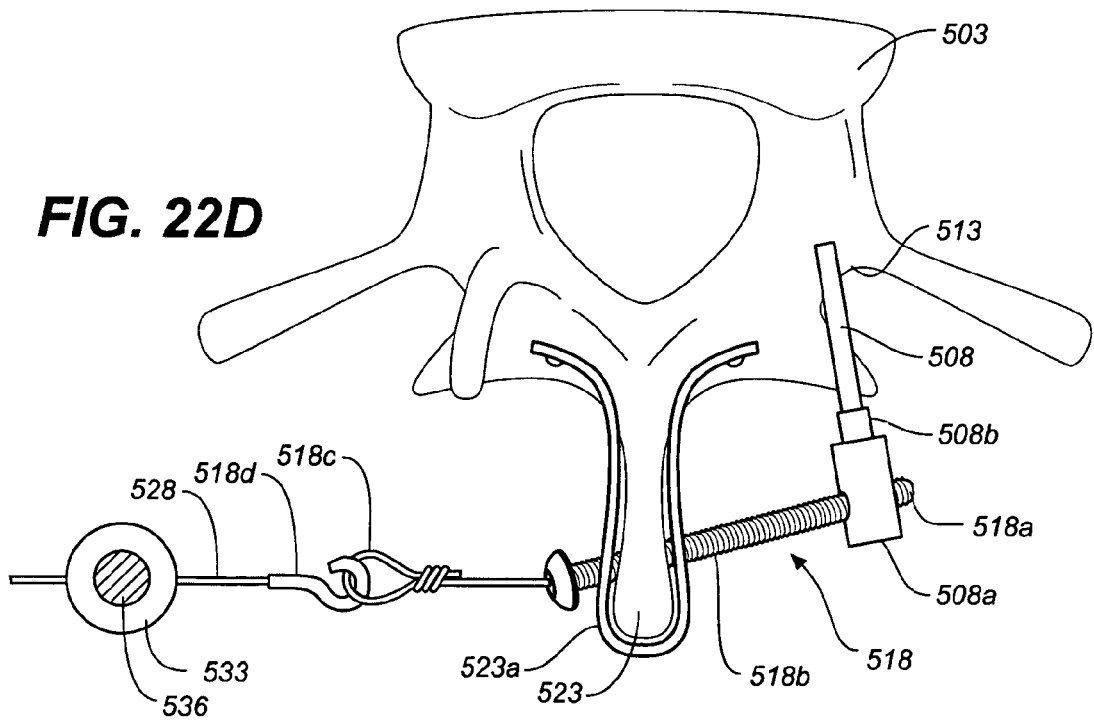
FIG. 22D is a schematic view of the adjustable pedicle attachment device of FIG. 22C in accordance with the invention.
Figure 22E:
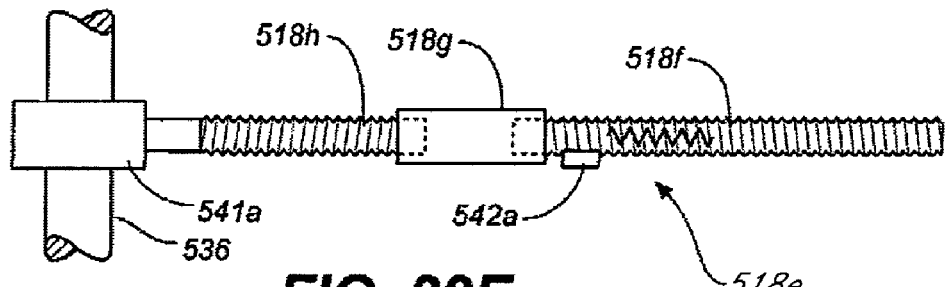
FIG. 22E is a schematic side partial cross sectional view of an alternative connector of the spine deformity device of FIG. 22A.
Figure 22F:
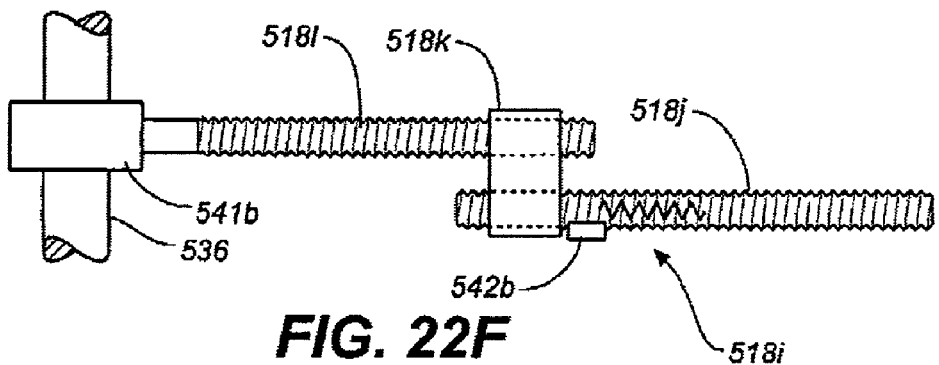
FIG. 22F is a schematic side partial cross-sectional view of an alternative connector of the spine deformity device of FIG. 22A.
Figure 22G:
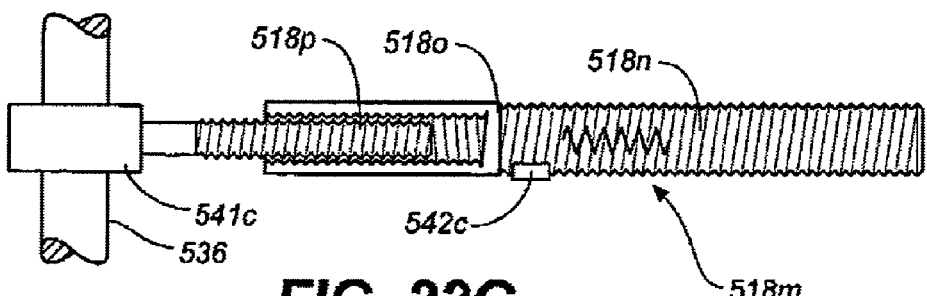
FIG. 22G is a schematic side partial cross sectional view of an alternative connector of the spine deformity device of FIG. 22A.
Figure 22H:
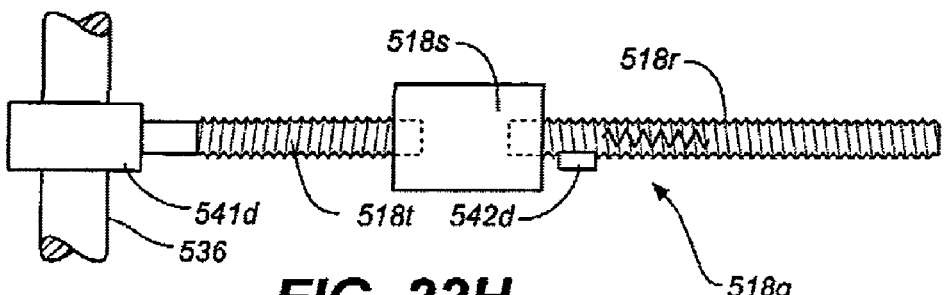
FIG. 22H is a schematic side partial cross sectional view of an alternative connector of the spine deformity device of FIG. 22A.
Figure 23A:
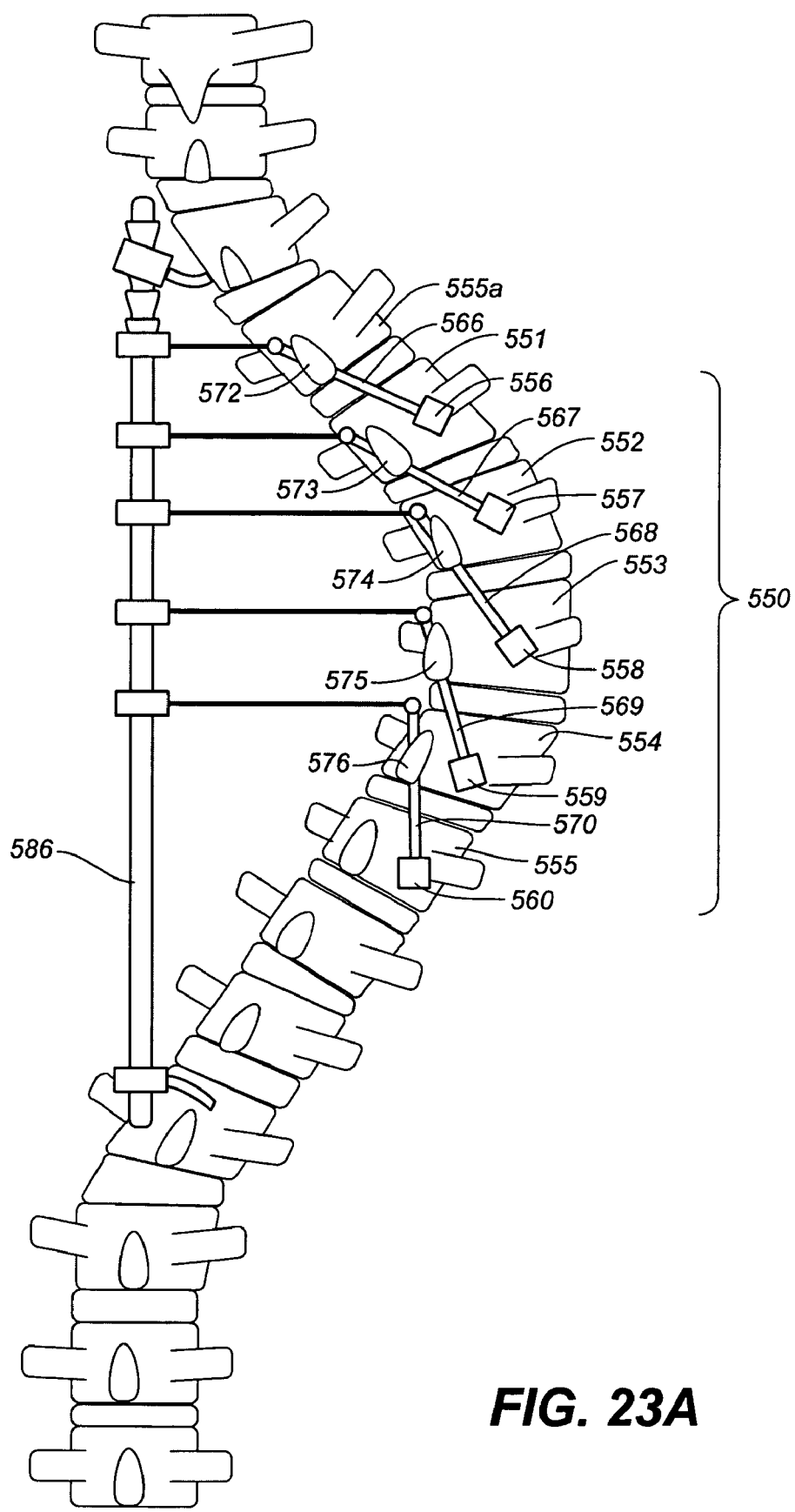
FIG. 23A is a schematic side view of a spine deformity correction device in accordance with the invention.
Figure 23B:
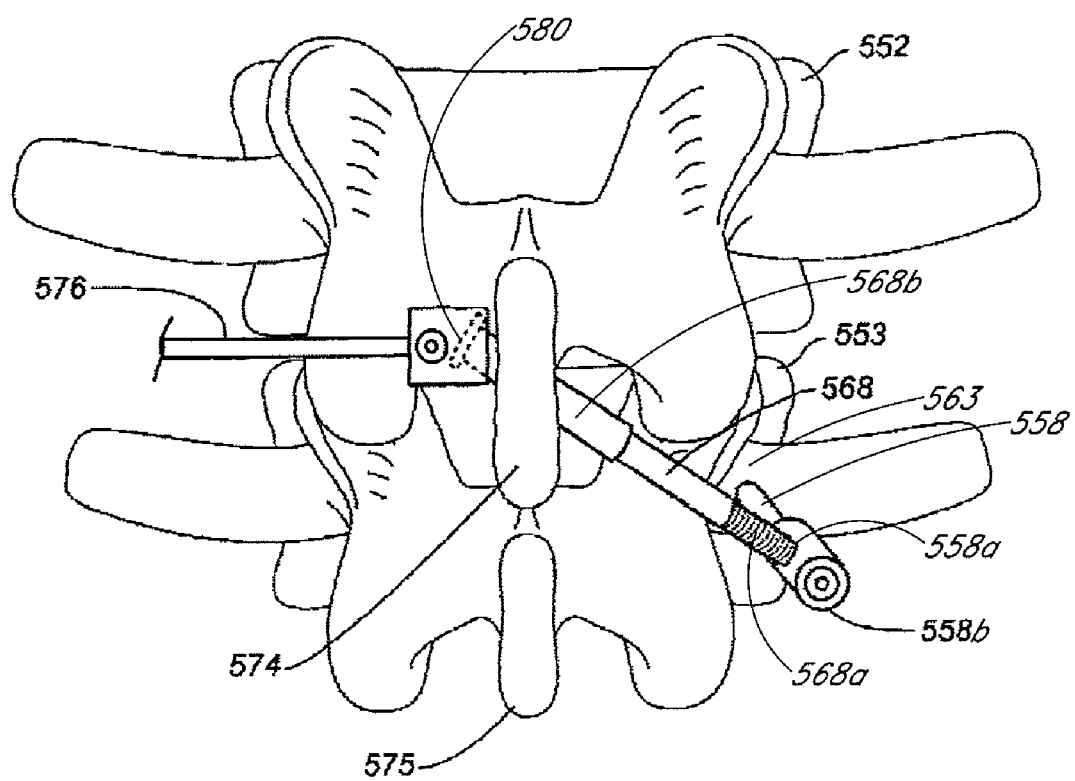
FIG. 23B is a posterior view.
Figure 24:
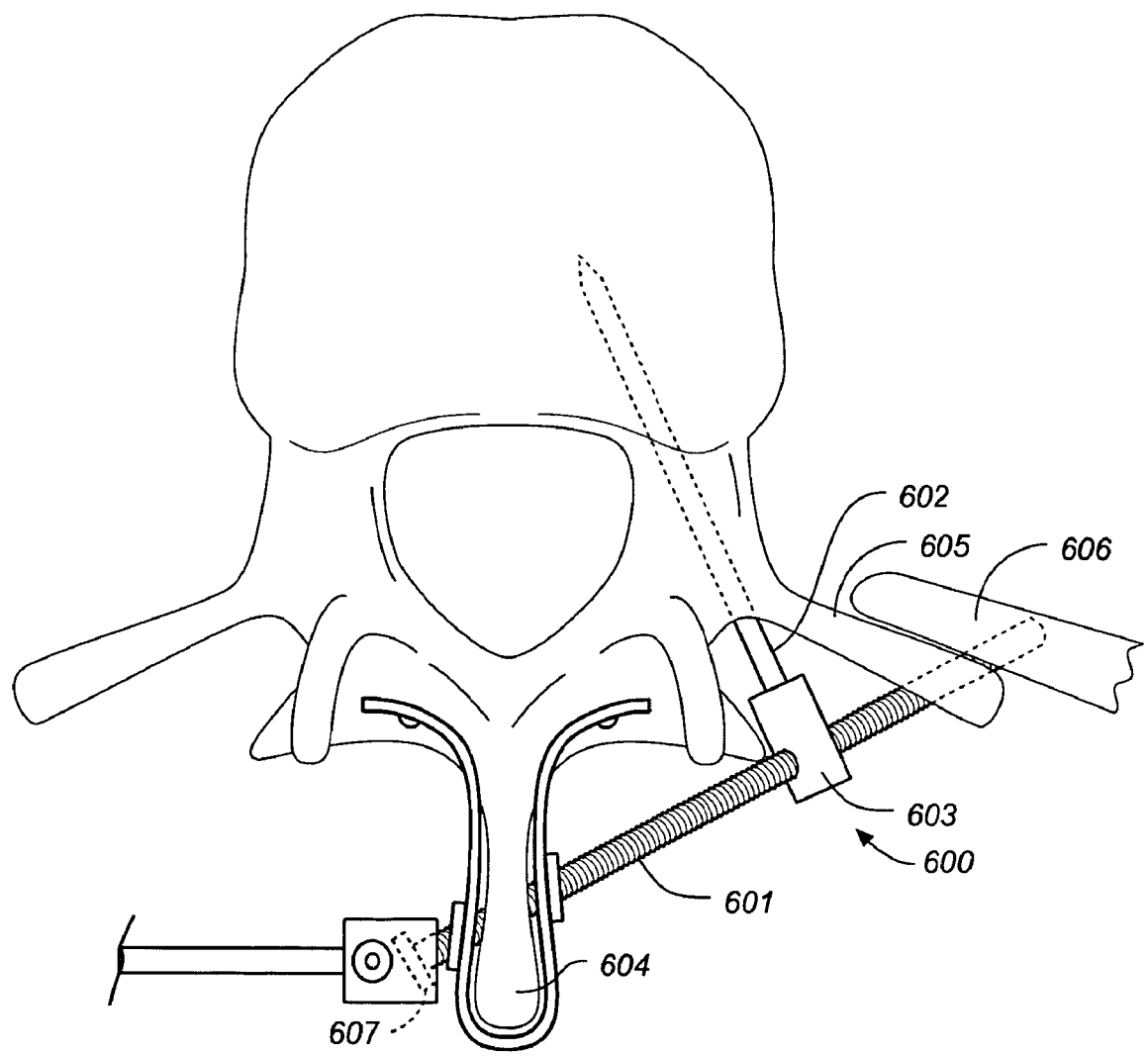
FIG. 24 is a schematic top view of an implant in accordance with the invention.

The systems illustrated in FIGS. 22A-24 comprise a multipoint anchoring mechanism that provides for multidimensional correction of the spinal or spinal segments by positioning the anchor at a plurality of locations on a spine. As illustrated for example in FIGS. 22A-22H, the multiple locations include the spinous process and pedicle of a particular vertebra. A bar is attached between the spinous process and pedicle. A force directing device couples the bar to a vertical rod. As illustrated in FIGS. 23A-23B, the multiple locations include the spinous process of one level and the pedicle of another level (e.g. an adjacent level). As illustrated in FIG. 24, the multiple locations include the spinous process, through a transverse process 605 into a costal aspect of a rib 606. The vertical rod in these figures is attached or coupled to the spine at neutral and balanced vertebra, typically only at the most upper and most lower positions.

The device comprises a telescoping rod (or plate) 536 to which various segments of the spinal column are to be fixed. The rod 536 telescopes to adjust the height to accommodate particular segments or a height of the spine. As illustrated in FIG. 22A a portion 500 of the spine comprises a plurality of adjacent segments 501, 502, 503, 504, 505, (additional adjacent segments may also be corrected). The portion 500 of the spine exhibits a concave curvature between segments 501 and 505. Pedicle screws 506, 507, 508, 509, 510 are attached to pedicles of segments 501, 502, 503, 504, 505, respectively. Dynamic stabilizers 516, 517, 518, 519, 520 are attached to pedicle screws 506, 507, 508, 509, 510 and to spinous processes 521, 522, 523, 524, 525 respectively of segments 501, 502, 503, 504, 505. Wires 526, 527, 528, 529, 530 attached to the rod 536 via hooks 531, 532, 533, 534, 535 attached to the rod 536. The wires 526, 527, 528, 529, 530 are used to tension the portion of the spine 500 to pull on the concavity. If the portion has a convexity, rods may be used in place of wires to push on the convexity to straighten the spine.

FIG. 22B is a cross section of FIG. 22A along the lines 22B-22B. The pedicle screw 508 includes a screw capture device 508a for receiving a screw head or rod of a dynamic stabilizer, in this case, a spinous process screw 518. The capture device may be a hole, a threaded screw hole with a washer or cap. The pedicle screw 508 may be configured to telescope outwards or inwards to be positioned to receive the screw head or rod of a dynamic stabilizer 518 as shown in FIGS. 22C and 22D. The spinous process screw 518 is shown in 22C where, given the trajectory of the spinous process screw 518, its end does not intercept the capture device 508a of the pedicle screw 508. As shown in FIG. 22D the pedicle screw's trunk 508b is lengthened with a telescoping or other similar lengthening mechanism so that the end of the spinous process screw 518 may be positioned in the capture device 508a.

The spinous process screw 518 is anchored through the reinforced spinous process 523 (having a reinforcement hood 523a or is otherwise reinforced as described herein. Note that the reinforcement hood may have a single lamina wing where a single screw is attached as opposed to bilateral screws.) with a head portion 518a engaging the pedicle screw 508 and a rod portion 518b (which may also be referred to as a lever member) extending through a reinforced spinous process 523. The dynamic stabilizer 518 includes (at what may be referred to as an attachment point) a loop connector end 518c for receiving a hook 518d of a wire (or a telescoping rod) 528 that is attached to the rod 536 with a ratcheted connector 533. The wire may also be a rod, spring, elastic band or other force-directing device (which may also be referred to as a force directing member). The loop connector end 518c may also be a poly axial connector that allows translation in a variety of directions or places, i.e., so that an oblique angle rod can be captured (for example, similar to pedicle screw 508 and capture device 508a). The wire 528 may be adjusted or tightened at various times with the ratcheted connector 533, e.g., during a period of time where the spine is being corrected. As the spine is straightened, excess wire may be trimmed off. This procedure may be done percutaneously, e.g. by accessing wire near the skin. Each dynamic stabilizer is similarly constructed.

FIGS. 22E-22H illustrate various dynamic stabilizers that may be used to correct spinal deformity. Dynamic stabilizers 518e, 518i, and 518m are coupled by coupling mechanisms 541a-c to the telescoping rod 536. The coupling mechanisms 541a-c may be positioned on or through the plate or telescoping rod 536. Dynamic stabilizer 518e includes rod 518f that will extend through a reinforced spinous process and is coupled (at what may be referred to as an attachment point) by a coupling mechanism 518g to rod 518h in an end-to-end fashion. Rod 518h slidably extends through opening in coupling mechanism 541a attached to the telescoping rod 536. The rod 518h is adjustable within the coupling mechanism 541a to lengthen or shorten the distance of the dynamic stabilizer 518e between the spinous process and the telescoping rod 536. The coupling mechanism 541a is configured to clamp down on the rod 518h to secure it in place once the distance has been adjusted. The coupling mechanisms 541a-c may include a screw, cam or clamp mechanism to clamp or lockably engage rods 518h, l, and p as described in use herein.

Similarly, dynamic stabilizer 518i includes rod 518j that will extend through a reinforced spinous process and is coupled (at what may be referred to as an attachment point) by a coupling mechanism 518k to rod 518l in an end to side fashion. Rod 518l slidably extends through opening in coupling mechanism 541b attached to the telescoping rod 536. The rod 518l is adjustable within the coupling mechanism 541b to lengthen or shorten the distance of the dynamic stabilizer 518i between the spinous process and the telescoping rod 536. The coupling mechanism 541b is configured to clamp down on the rod 518l to secure it in place once the distance has been adjusted.

Dynamic stabilizer 518m includes a rod 518n that will extend through a reinforced spinous process and is coupled (at what may be referred to as an attachment point) by a threaded coupling 518o to rod 518p. The rod 518p is slidably and rotatably positioned within a cylindrical hole in coupling mechanism 541c attached to the telescoping rod 536. The rod 518p may be rotated, i.e., screwed or unscrewed so that the stabilizer lengthens or shortens at the threaded coupling 518o. The rotation or screwing may be actuated at or near the skin where the rod 518p is positioned in the coupling mechanism 541c.

Dynamic stabilizer 518q includes a rod 518r that will extend through a reinforced spinous process and is coupled (at what may be referred to as an attachment point) by a multiaxial coupling 518s similar to a multiaxial screw head type coupling, to rod 518t. The rod 518t is a telescoping rod and is coupled by coupling mechanism 541d to the vertical rod 536.

Each of the dynamic stabilizers may include sensors located thereon to sense data corresponding to a parameter of the dynamic stabilization device or the spine. FIG. 22E-22H illustrate sensors 542a-542d located on the dynamic stabilizer. The sensors may comprise, e.g., a strain, stress, pressure, position or motion sensor. Such sensors may include a variety of sensors that are generally know. For example, strain gauges, accelerometers or piezo electric sensors may be employed to sense parameters that correspond, e.g., to the position of the spine, a vertebra, a dynamic stabilizer, as well as the parameters relating to the forces or mechanical loads that are effecting the device. Each of the sensors may individually sense information or information relative to each of the other sensors may be sensed and compared. The information may be used to set tension on the device, to identify when repositioning is necessary or to otherwise provide information as to the status of the device or portions thereof, or status of the spine that is being treated. The sensors may include some level or circuitry including, e.g. a telemetry circuit that transmits information concerning the sensors to an external device. The sensors may be battery powered or may use passive circuits that are powered by an external device. The information may be used to identify when one of the stabilizers no longer has tension associated with the stabilizer thus identifying when the tension needs to be modified in the device. Accordingly, each segment may be moved separately, monitored separately and adjusted separately form the other segments. Each segment may be moved to a different degree and in different directions or at different angles with varying forces.

FIG. 23A illustrates an alternative configuration of the correction device according to the invention. A portion 550 of the spine comprises a plurality of adjacent segments 551, 552, 553, 554, 555, 555a (additional adjacent segments may also be corrected). The portion 550 of the spine exhibits a concave curvature between segments 551 and 555a. Pedicle screws 556, 557, 558, 559, 560 are attached to pedicles of segments 551, 552, 553, 554, 555, respectively. Dynamic stabilizers 566, 567, 568, 569, 570 are attached to pedicle screws 556, 557, 558, 559, 560 and through spinous processes, 572, 573, 574, 575, 576 respectively of adjacent segments 555a, 551, 552, 553, 554. Thus, the dynamic stabilizers are positioned across the motion segments between the corresponding adjacent segments. The dynamic stabilizers 566, 567, 568, 569, 570 attached to the telescoping rod 576 in one or more manners such as, for example, the dynamic stabilizers 518, 518e, 518i, 518m, 518q as illustrated in FIGS. 22A-22H, herein. The dynamic stabilizers 566, 567, 568, 569, 570 are used to tension the portion of the spine 500 to pull on the concavity, or if the portion has a convexity, to push, pull on, or translate the convexity to straighten the spine. Thus each of the dynamic stabilizers are attached a plurality of locations on the spine and operate to stabilize adjacent segments with respect to each other.

FIG. 23B illustrates a pedicle screw and dynamic stabilizer (which may be referred to together as a vertebral connector) in greater detail. The pedicle screw 558 is screwed into pedicle 563 of vertebra 553. The pedicle screw 558 includes a screw hole 558a for receiving a screw head or rod of a dynamic stabilizer 568. A screw capture device 558b such as a nut or a threaded portion of the pedicle screw is configured to capture and receive the dynamic stabilizer screw or head portion 568a. The capture device 558b of the stabilizer engages the pedicle screw 558 and a rod portion 568b extends through a reinforced spinous process 574. The dynamic stabilizer 568 includes a connector end 580 (at what may be referred to as an attachment point) for receiving a wire or a hook of a telescoping rod that is attached to a telescoping rod 576. The dynamic stabilizer 568 is anchored through the reinforced spinous process 574 of an adjacent vertebra 552 (FIG. 23A) thus immobilizing or stabilizing the motion segment between the vertebra 552, 553. This device may also be used in fusion, i.e. to fuse the motion segments across vertebra of a multipoint connector. The device may also be used to encourage overgrowth at certain locations. In particular it may encourage overgrowth on the non-fused lateral side of a vertebra (opposing the fused lateral side) stabilized with the multipoint connector between two vertebrae.

FIG. 24 illustrates a device for treating a deformity such as scoliosis. The device includes a dynamic stabilizer 600 comprising a spinous process screw 601 and a pedicle screw 602 including a spinous process screw capture device 603. The spinous process screw is configured to be positioned through a reinforced spinous process 604 and through a transverse process 605 into a costal aspect of a rib 606. The dynamic stabilizer 600 includes a connector portion 607 configured to be connected to a telescoping rod as described herein with reference to FIGS. 22A-H and 23A-23B. Similar to FIGS. 22A-H and 23A-23B, a plurality of segments may be secured to a telescoping rod with a plurality of dynamic stabilizers. The pedicle screw in this and all other embodiments described in this application may include a telescoping portion that can adjust the length of the screw head from the anchoring point where the pedicle screw is anchored into the bone. The pedicle screw 602 also includes a sensor located thereon (or incorporated therewith). The sensor may comprise, for example, a motion detector, a position detector, a pressure sensor, a strain gauge, and ultrasonic transducer/sensor. The sensor may sense a change in strain on the screw that may be due to loosening or repositioning of the screw. The sensor may also sense a change in position of the screw that indicates a change in alignment and corresponding loosening or repositioning of the screw. The sensor may also sense a change in pressure due to loosening or repositioning of the screw. The sensor may also include an ultrasonic transducer and transmitter that can determine change in positioning of the screw, e.g. loosening of the screw indicated by a change in interfaces of materials or characteristic property change indicating screw loosening or repositioning. The sensor may include some electronics such as a telemetry circuit that allows it to communicate with an external device. The sensor may also be powered by an external device e.g., in a manner generally known in the art.

The various embodiments of the invention described herein may include sensors integrated with or provided on a structural spinal implant. A number of factors may be detected as described herein. Additional factors may include, e.g., local inflammation, pressure, tension, edema, motion, water content, and electrolytes or other chemicals. The sensors allow a doctor to monitor patients for response to healing, or may be used by the doctor to guide serial adjustments to the patient's treatment. For example, measurements from the sensing means could lead the doctor to change the length or tension of a distraction rod or stabilization device. Patients could adjust therapy based on measurements from the sensing device, or could be alerted to notify their doctor should certain measurements be of concern. The sensor is configured to be adjustable to sensed stresses. The sensor may for example, be a strain gauge, a pressure sensor accelerometer, position sensor, imaging device, etc. The sensor may be used in the initial adjustment of the prosthesis or may be monitored over time. The sensor may sense shear/torsion tension/compression. Sensors may sense stresses at various motion segments. The sensor may be used to compare stresses at various motion segments or locations. Various sensors may be selected from sensors that are known to one of skill in the art or that are commercially available.

Anchoring of Therapeutic Devices

Some patients obtain back pain relief with injections of steroids and anesthetic agents at the site of pain; however the relief is temporary requiring that patients return for repeat injections when their pain recurs.

One embodiment of the invention comprises an anchor device with a therapeutic substance or drug delivery device, e.g. a drug port and/or reservoir, or matrix attached to a vertebra. In one embodiment, the device is anchored adjacent a site near where pain is present. The port is configured to deliver steroids or anesthetic agents via a catheter to a desired location, for example, the facet joint, neural foramen, vertebral body, annulus, nucleus, back muscles, back ligaments, bone metastases, intrathecal space, epidural space, or other targets in, on, or around the spine. The catheter can direct the drug to the correct location by positioning the end of the catheter at a target location. The port is configured to be refilled periodically percutaneously, e.g. using an imaging device and a percutaneously placed needle that can inject the refill into the port, e.g. through a biocompatible polymer or rubber type port access mechanism. The device further comprises a patient actuation mechanism for patient control of drug delivery as needed for pain relief, manually or remotely using a telemetrically triggered delivery from an external telemetry control device. According one aspect of the invention such a device is attached to a boney structure of the spine. Other device that may be attached to the spine may include sensory or therapeutic devices, including nerve stimulators, bone growth stimulators and radioactive seeds.

In addition, a structural implant could be anchored to bone, to which a sensory or therapeutic device could be attached. The sensory or therapeutic device could be placed external to the bone, on the surface of the bone, or internal to the bone.

Figure 25:
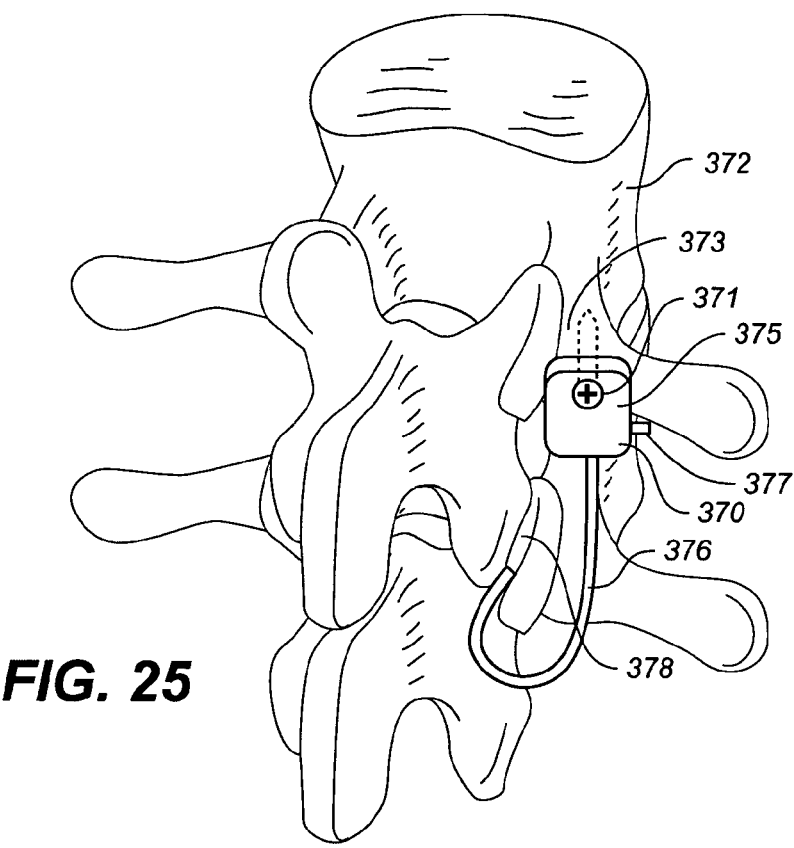
FIG. 25 is a schematic posterior lateral perspective view of a therapeutic substance delivery device in accordance with the invention.
Figure 26:
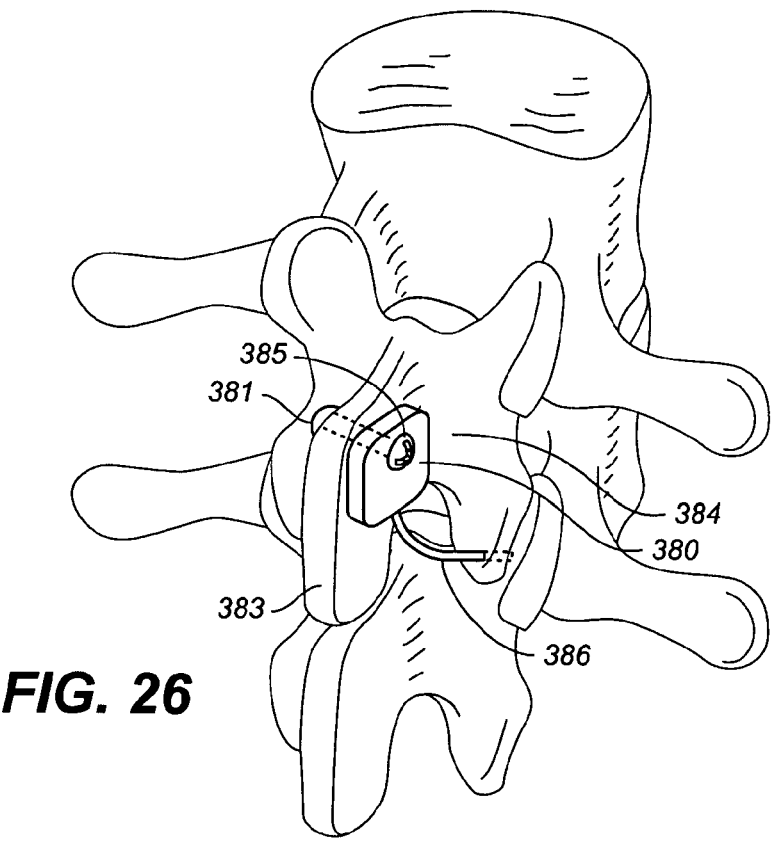
FIG. 26 is a schematic posterior lateral perspective view of a therapeutic substance delivery device in accordance with the invention.

FIGS. 25 and 26 illustrate drug delivery devices 370, 380, respectively, in accordance with the invention. The drug delivery device 370 includes a reservoir 375 attached by an anchor 371 configured to anchor the reservoir 375 to the bone of the spine. In particular, in this embodiment, the anchor 371 comprises a pedicle screw that anchors the device to the pedicle 373 of a vertebra 372. The reservoir 375 includes a catheter 376 in communication with the contents of the reservoir 375 and having an end positioned adjacent or in a zygapophyseal joint 378 where the drug is directed to have a therapeutic effect on the joint 378. The device may include a telemetrically actuable pump mechanism for delivering the drug to the joint upon telemetric actuation by an external control device. The device 370 further comprises a port 377 for receiving (e.g. via a percutaneously introduced needle) into the reservoir 375, refills of the therapeutic substance or drug. Device 380 comprises a similar catheter 386, and reservoir 385 attached by an anchor 381 to the spinous process 383 or alternatively an adjacent lamina 384. The spinous process 383 or lamina 384 may be reinforced prior to attachment of the anchor 381 or may be attached to a reinforcement device positioned at the posterior arch of the spine, as described herein with reference to FIGS. 1A-7B.

What is claimed is:

1. A method for correcting a spinal deformity in a patient, the deformity characterized by vertebral translation and rotation, the method comprising:
   implanting a rod generally parallel to and on a first lateral side of the patient's spine;
   attaching a connector to a vertebra of the patient at a fixation point on a second side of the patient's spine opposite to the first side, wherein the connector includes an attachment point spaced apart laterally from the fixation point;
   pulling the vertebra toward the rod by applying tension to a force-directing member extending from the rod to the attachment point; and thereafter
   adjusting the tension on the force-directing member.

2. The method of claim 1, wherein:
   the attaching step comprises attaching a plurality of said connectors to a plurality of the vertebrae of the patient;
   the pulling step comprises pulling the plurality of vertebrae toward the rod by applying tension to a plurality of force-directing members, each said force-directing member extending individually from the rod to a different said attachment point on a different vertebra; and
   the adjusting step comprises adjusting the tension on at least some of the plurality of force-directing members.

3. The method of claim 2, wherein the adjusting step comprises separately adjusting force directing members to apply a different tension to one force-directing member than is applied to another force-directing member.

4. The method of claim 3, further comprising adjusting the tension on a force-directing member by shortening the length of the force-directing member between the rod and the attachment point.

5. The method of claim 2, wherein the plurality of said force-directing members extend, respectively, from separate points along the rod in a generally orthogonal direction directly from the rod to the attachment point.

6. The method of claim 1, wherein the attachment point is rigidly connected to the fixation point and is located on the first side of the spine extending out from the vertebra, further comprising applying an oblique tension force to the attachment point with the force directing member to apply both a translational and derotational force to the vertebra.

7. The method of claim 1, wherein the pulling step comprises both translating and derotating the vertebra.

8. The method of claim 1, further comprising fixing the connector to at least first and second fixation points on the second side of the patient's spine.

9. A method for correcting a spinal deformity in a subject, the deformity characterized by vertebral translation and rotation, the method comprising:
   providing a connection device;
   providing a rod having a longitudinal axis extending generally vertically parallel to the sagittal plane of a patient's body;
   connecting the connection device to at least one location on a first vertebra;
   coupling a force directing member to an attachment point of the connection device; the attachment point being spaced apart laterally from the at least one location on the first vertebra;
   coupling the force directing member to the rod at a position along the rod generally orthogonal to the first vertebra; and
   applying a corrective derotating and translating force to the first vertebra through the force directing member and the connection device.

10. The method of claim 9, wherein the at least one location comprises a location on a spinous process of the first vertebra.

11. The method of claim 9, wherein the at least one location comprises a pedicle of the first vertebra.

12. The method of claim 9, further comprising connecting the connection device to a second location on the first vertebra.

13. The method of claim 9, further comprising connecting the connection device to a second vertebra.

14. The method of claim 13, wherein the connection device is configured to fuse the first and second vertebrae.

15. The method of claim 9, wherein the connection device is configured to encourage overgrowth of the first vertebra.

16. The method of claim 9, further comprising adjusting the corrective force.

17. The method of claim 16, wherein the step of adjusting the corrective force is performed after the connecting and coupling steps.

18. The method of claim 16, further comprising maintaining the adjusted corrective force.

19. The method of claim 9, wherein the force directing member and the connection device are movable with respect to one another at a plurality of angles.

20. The method of claim 9, further comprising connecting a plurality of said connection devices, respectively, to a plurality of vertebrae.

21. The method of claim 20, further comprising coupling each force directing member to the rod at a different position along the rod.

22. The method of claim 20, further comprising adjusting a length of a first force directing member independently of a length of a second force directing member.

23. The method of claim 9, wherein the rod is provided on a first side of the spine.

24. The method of claim 23, wherein the at least one location is on a second side of the spine.

25. The method of claim 23, wherein the attachment point is on a second side of the spine.

26. A method of correcting a spinal deformity in a subject, the method comprising:
    establishing a desired orientation of vertebrae in a spine using a vertically-extending rod;
    engaging a vertebra at a fixation point using a vertebral connector, the vertebral connector having an attachment point spaced apart laterally from the fixation point; and
    applying both a derotating force and a translating force to the vertebra using a force directing member coupled to the rod and to the attachment point.

27. A method of correcting a spine exhibiting an abnormal curvature, the spine having an upper vertebra, a lower vertebra, and an intermediate vertebra, the intermediate vertebra having a translational and rotational orientation and being located between the upper and lower vertebrae, the method comprising:
    securing a first rod anchor to the upper vertebra and a second rod anchor to the lower vertebra;
    positioning a rod along a first side of the spine by coupling a first portion of the rod to the first rod anchor and a second portion of the rod to the second rod anchor;
    securing a vertebral anchor to the intermediate vertebra by coupling the vertebral anchor to a posterior location on a second side of the spine opposite the first side of the spine;
    securing a first end of a lever member to the vertebral anchor such that a second end of the lever member projects laterally away from the vertebral anchor toward the first side of the spine;
    securing the second end of the lever member to a force directing member;
    securing the force directing member to the rod to form a connection between the rod and the intermediate vertebra; and
    adjusting a length of the connection between the rod and the intermediate vertebra to alter the rotational and translational orientation of the intermediate vertebra.

28. The method of claim 27, wherein the connection between the rod and the intermediate vertebra includes a wire and further wherein adjusting the length of the connection includes tensioning the wire.

29. The method of claim 27, wherein securing the force directing member to the rod includes forming a multi-angle connection between the rod and the intermediate vertebra.

30. The method of claim 27, wherein the length of the connection is adjusted to stabilize the intermediate vertebra at a corrected rotational and translational orientation.

31. The method of claim 27, further comprising forming a second connection between a second intermediate vertebra and the rod and, independently from the length of the first connection, adjusting a length of the second connection to alter a rotational and translational orientation of the second intermediate vertebra.

32. The method of claim 27, wherein the abnormal curvature has a convex aspect and a concave aspect, the second side of the spine corresponding to the concave aspect of the curvature, wherein the rod is positioned along the convex aspect of the abnormal curvature, and wherein the intermediate vertebra is corrected to a derotated and translated orientation by increasing the length of the connection to push on the convex aspect of the abnormal curvature.

33. The method of claim 27, wherein the abnormal curvature has a convex aspect and a concave aspect, the second side of the spine corresponding to the convex aspect of the curvature, wherein the rod is positioned along the concave aspect of the abnormal curvature, and wherein the intermediate vertebra is corrected to a derotated and translated orientation by decreasing the length of the connection to pull on the concave aspect of the abnormal curvature.

34. The method of claim 27, further comprising securing a coupling mechanism to the rod, wherein securing the force directing member to rod includes securing the force directing member to the coupling mechanism, and further wherein adjusting a length of the connection includes adjusting the length of the force directing member with the coupling mechanism.

35. The method of claim 27, wherein securing the second end of the lever member to the force directing member includes forming a multi-angle connection.

36. The method of claim 27, wherein the upper and lower vertebrae are neutral and balanced vertebrae proximate an upper end and a lower end, respectively, of the abnormal curvature.

* * * * *

UNITED STATES PATENT AND TRADEMARK OFFICE
CERTIFICATE OF CORRECTION

Page 1 of 1

PATENT NO.         : 8,043,345 B2
APPLICATION NO.    : 12/645305
DATED              : October 25, 2011
INVENTOR(S)        : Allen L. Carl and Dan Sachs It is certified that error appears in the above-identified patent and that said Letters Patent is hereby corrected as shown below:

At Column 1, Line 32, please change "honey" to --boney--.

At Column 5, Lines 38-40, below "position.", please delete "FIG. 4B is a posterior lateral perspective view of a distraction system implanted in a spine in accordance with the invention.".

Signed and Sealed this
Tenth Day of July, 2012

David J. Kappos
*Director of the United States Patent and Trademark Office*